United States Patent
Kotz et al.

(10) Patent No.: US 10,139,333 B2
(45) Date of Patent: Nov. 27, 2018

(54) SYSTEM AND METHOD FOR INERTIAL FOCUSING CYTOMETER WITH INTEGRATED OPTICS FOR PARTICLE CHARACTERIZATION

(71) Applicants: THE GENERAL HOSPITAL CORPORATION, Boston, MA (US); Kenneth T. Kotz, Auburndale, MA (US); Ramin Haghgooie, Arlington, MA (US); Anne C. Petrofsky, Sudbury, MA (US); Robert Granier, Boston, MA (US); Ronald G. Tompkins, Boston, MA (US)

(72) Inventors: Kenneth T. Kotz, Auburndale, MA (US); Ramin Haghgooie, Arlington, MA (US); Anne C. Petrofsky, Sudbury, MA (US); Robert Granier, Boston, MA (US); Ronald Tompkins, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/032,463

(22) PCT Filed: Oct. 27, 2014

(86) PCT No.: PCT/US2014/062426
§ 371 (c)(1),
(2) Date: Apr. 27, 2016

(87) PCT Pub. No.: WO2015/065909
PCT Pub. Date: May 7, 2015

(65) Prior Publication Data
US 2016/0252447 A1 Sep. 1, 2016

Related U.S. Application Data

(60) Provisional application No. 61/897,339, filed on Oct. 30, 2013.

(51) Int. Cl.
*G01N 15/14* (2006.01)
*G01N 21/64* (2006.01)
(Continued)

(52) U.S. Cl.
CPC ..... *G01N 15/1436* (2013.01); *G01N 15/1404* (2013.01); *G01N 15/1459* (2013.01);
(Continued)

(58) Field of Classification Search
CPC .......... G01N 15/1404; G01N 15/1436; G01N 15/1459; G01N 15/1484;
(Continued)

(56) References Cited

U.S. PATENT DOCUMENTS

| 2003/0054558 A1 | 3/2003 | Kurabayashi et al. |
| 2005/0014248 A1 | 1/2005 | Canton |

(Continued)

OTHER PUBLICATIONS

Goodman. Chapter 1, General Principles of Geometric Optics, s Part 1. Geometric Optics 1 1, Handbook of Optics, vol. 1, Fundamentals, Techniques, and Des:gn, Bass (ed), McGraw-Hill, pp. 1.1-1.109 (1995), p. 1 1.27-1.39, Equations 110-123.*

(Continued)

*Primary Examiner* — Jennifer Wecker
(74) *Attorney, Agent, or Firm* — Quarles & Brady LLP

(57) ABSTRACT

The present invention provides a microfluidic system, device, and kit for particle analysis. In one example, the device includes a fluid channel for spacing the particles, an excitation waveguide to guide an excitation beam from a source to the fluid channel, and an excitation lens to focus the excitation beam to a width less than the spacing of the particles in the fluid channel. The device also includes a detection lens to guide light transmitted from the channel along a number of paths, axial and scatter light waveguide to receive light guided by the detection lens, a detector to (Continued)

receive transmitted light from the waveguides and generate a detection signal, and a processor configured to receive the detection signal and determine characteristic features of each of the particles based on the detection signal.

23 Claims, 18 Drawing Sheets

(51) Int. Cl.
    *B01L 3/00*     (2006.01)
    *G01N 15/10*     (2006.01)
    *G01N 15/00*     (2006.01)

(52) U.S. Cl.
    CPC ..... *G01N 15/1484* (2013.01); *G01N 21/6428* (2013.01); *G01N 2015/008* (2013.01); *G01N 2015/0073* (2013.01); *G01N 2015/0084* (2013.01); *G01N 2015/1006* (2013.01); *G01N 2015/1486* (2013.01); *G01N 2021/6439* (2013.01); *G01N 2201/0638* (2013.01)

(58) Field of Classification Search
    CPC ..... G01N 2015/0073; G01N 2015/008; G01N 2015/0084; G01N 2015/1006; G01N 2015/1486; G01N 2021/6439; G01N 21/6428; G01N 2201/0638
    See application file for complete search history.

(56) References Cited

U.S. PATENT DOCUMENTS

| | | | |
|---|---|---|---|
| 2009/0027666 A1* | 1/2009 | Godin | B01L 3/502776 356/246 |
| 2009/0155832 A1* | 6/2009 | Lo | B01L 3/502707 435/29 |
| 2011/0007261 A1 | 1/2011 | Abbott et al. | |
| 2011/0008787 A1 | 1/2011 | Durack | |
| 2013/0217583 A1* | 8/2013 | Link | B01F 13/0071 506/2 |

OTHER PUBLICATIONS

International Search Report and Written Opinion dated Apr. 1, 2015 in connection with PCT/US2014/062426.

Tsao et al, Bonding of thermoplastic polymer microfluidics, Microfluid Nanofluid (2009) 6:1-16, published online Nov. 13, 2008 (Nov. 13, 2008), Abstract, p. 2., col. 1-2, Table 1.

Goodman, Chapter 1, General Principles of Geometric Optics,s Part 1. Geometric Optics 1.1, Handbook of Optics, vol. 1, Fundamentals, Techniques, and Design, Bass (ed), McGraw-Hill, pp. 1.1-1.109 (1995), p. 1.27-1.39, Equations 110-123.

* cited by examiner

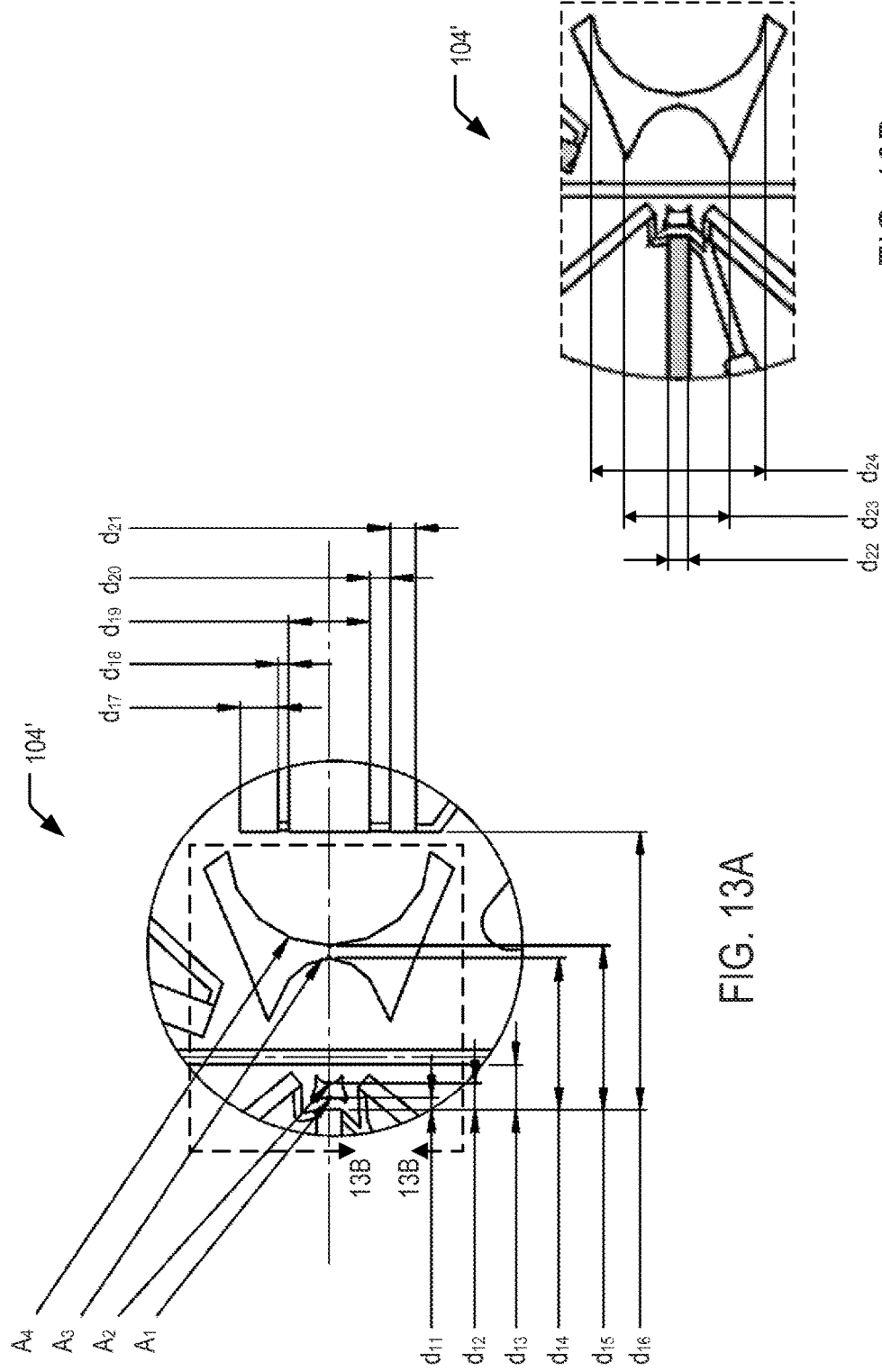

SYSTEM AND METHOD FOR INERTIAL FOCUSING CYTOMETER WITH INTEGRATED OPTICS FOR PARTICLE CHARACTERIZATION

CROSS-REFERENCE TO RELATED APPLICATIONS

This application is a 371 application of PCT/US2014/062426 filed Oct. 27, 2014 which claims the benefit of U.S. Provisional Application No. 61/897,339 filed Oct. 30, 2013, which are incorporated herein by reference for ail purposes.

STATEMENT REGARDING FEDERALLY SPONSORED RESEARCH

This invention was made with government support under United States National Institutes of Health grant numbers U54 GM-062119 and P41 EB-002503. The government has certain rights in the invention.

BACKGROUND OF THE INVENTION

The disclosure relates, in general, to the design and construction of an optofluidic device and, more particularly, to an optical cytometer for cell counting.

Continuous manipulation and separation of microparticles, both biological and synthetic, is important for a wide range of applications in industry, biology, and medicine. Traditional techniques of particle manipulation rely on laminar flow or differences in either particle mobility or equilibrium position in a flow with a variety of externally applied forces. Recently, microfluidic systems have been shown to be very useful for particle handling with increased control and sensitivity. Systems have been demonstrated that use scale-dependent electromagnetic forces, microscale hydrodynamic effects, or deterministic physical interactions and filters. However, the precision of microfluidic systems based on deterministic interaction with walls or posts may be limited by disturbances from random interparticle contact and spacing, and mechanical systems are prone to clogging. Additionally, throughput for particle manipulation based on external forces has been limited because the time for forces to act decreases with increasing flow rate.

It has been recently demonstrated that inertial lift forces in laminar microfluidic systems can be used to focus randomly distributed particles continuously and at high rates to a single streamline. In one aspect, this process is primarily controlled by the ratio of particle size to channel size and the flow characteristics of the system, but can be independent of particle density. This simple and robust method requires no mechanical or electrical parts, making it desirable for a number of applications.

One application of particular interest is flow cytometry, which is a common method for the analysis of cells and particles in biomedical research and clinical diagnostics. Current flow cytometers are large, robust bench top instruments capable of measuring optical scattering and fluorescence of cells and particles at extremely high throughput (~1000's of events per second). While these systems have decreased in size over time, they are still not amenable to mobile point of care diagnostic settings or rugged environments due to the size and sensitivity of the measurement optics.

Integration of microscale fluidic and optical technologies is a promising approach for reducing the size and complexity of optical cytometers. Current approaches to optofluidic integration typically employ optical waveguides to direct light to a microfluidic flow cell, with many different design approaches for both the optical and fluidic system. Most designs employ either optical fibers to directly deliver light to a flow cell or slab waveguiding structures that employ photolithographic materials to guide light to a fluid channel defined within the slab. While using optical fibers directly is an attractive method because of the cost, availability, and excellent properties of commercial fibers, it does not allow shaping of the excitation or scattered light. Accordingly, such systems struggle with the discrimination of particles based on scattering because contamination from the excitation source can quickly mask the smaller scattering signals.

Systems that employ slab waveguides are an attractive alternative to direct insertion of fibers into microfluidic structures. Slab waveguides are formed by sandwiching a patterned material with a high refractive index between two substrates with a lower index of refraction. These systems are attractive because of the precision of photolithographic patterning of surface features that act as waveguiding structures. Slab waveguides have been used to optimize excitation beam shape, steer excitation light with total internal reflection, and collect scattered light. These systems, however, typically involve complex construction methods, require photolithographic patterning for each device, and employ materials that can autofluoresce or degrade with ultra-violet exposure.

Therefore, what is needed is an easily manufactured, microfluidic device that is capable of (i) controlling the spatial distribution of particles, (ii) analyzing the particles, and (iii) supporting mobile point-of-care diagnostics. It would also be desirable to achieve these capabilities in a cost-effective manner to enable true point-of-care diagnostics, particularly, in situations where cost is a driving consideration, such as in developing nations.

SUMMARY OF THE INVENTION

The present invention overcomes the aforementioned drawbacks by providing a microfluidic device that uses a plurality of waveguides coupled with an arrangement of lenses. In one aspect, the present invention exploits inertial focusing in a compact, integrated device with an optical system that focuses the excitation beam to a width narrower than the interparticle spacing. Optical lenses collimate the excitation beam and remove it from detectors that measure scattered light. Thus, a highly-controllable system is created that leverages the advantages of using waveguides in a manner that is efficient and cost effective. In addition, various aspects of the present invention can be coupled with traditional components of a flow cytometry system. For example, using waveguides to control either forming of the excitation light or the collection of scattered light from particles in the microfluidic channel while using traditional free space optics for the detection or excitation respectively.

In accordance with one aspect of the present disclosure, a microfluidic device is provided for analysis of a plurality of particles. The device includes a fluid channel having a geometry configured to effect a predetermined spacing of the particles. The device also includes an excitation waveguide configured to receive an excitation beam from a source to provide the excitation beam to the fluid channel, an excitation lens arranged to receive the excitation beam directed toward the fluid channel and focus the excitation beam to a predetermined width that is less than the predetermined spacing of the particles in the fluid channel to induce an interaction between the excitation beam and the particles resulting in a transmitted light, and a detection lens arranged relative to the transmitted light to guide the transmitted light along a plurality of paths. The device further includes at least one scattered light waveguide to receive light scattered by the particles, an axial light loss waveguide to receive light guided by the detection lens along at least one of the plurality of paths and not received by the at least one forward scatter waveguide, and a detector arranged to receive transmitted light from the at least one forward scatter waveguide and from the axial light loss waveguide and generate a detection signal based thereon. Another component of the device is a processor configured to receive the detection signal and determine characteristic features of each of the plurality of particles based on the detection signal.

In one aspect, the scattered light waveguide includes at least one forward scatter waveguide to receive light guided by the detection lens along at least one of the plurality of paths. In another aspect, the scattered light waveguide comprises at least one side scatter waveguide to receive light at a high scatter angle relative to the optical axis of the system and greater than the angles collected by the at least one forward scatter and axial light loss waveguides.

In one aspect, at least one surface of the excitation lens and detection lens is an aspheric surface and in another aspect, the particles are biological molecules. In yet another aspect, the biological molecules can be red blood cells, white blood cells, or platelets. In another aspect, the particles can be fluorescently labeled or unlabeled biological molecules, fluorescent particles, synthetic microparticles, polymer microspheres and/or magnetic microspheres.

In still another aspect, a transverse cross-section of the fluid channel is rectangular and in another aspect, the waveguides are step-index waveguides including a first and second material, where the refractive index of the first material is greater than the refractive index of the second material. In still another aspect, the predetermined spacing of the particles is effected by inertial focusing.

In one aspect, the excitation waveguide, the forward scatter waveguide, and the axial light loss waveguide are formed using a high refractive index polymer. In another aspect, a cladding material forming a substrate of a cycloolefin thermoplastic (COP) is configured to at least one of form and support the fluid channel, the excitation waveguide, the at least one scattered light waveguide, and the axial light loss waveguide. In still another aspect, at least one of the excitation lens and the detection lens includes a surface defined by the equation:

$$z(r) = \frac{cr^2}{1 + \sqrt{1 - (1+k)c^2 r^2}} + \sum_{i=4,6,8,\ldots} A_i r^i;$$

where z(r) is a surface profile as a function of distance off an optical axis, r, of the at least one of the excitation lens and the detection lens surface curvature, c is an inverse of a spherical radius of curvature of the at least one of the excitation lens and the detection lens, k is a conic constant, and $A_i$ are higher order aspheric terms.

In accordance with another aspect of the present invention, a microfluidic device is provided for analysis of a plurality of particles. The device includes a fluid channel having a geometry relative to the plurality of particles configured to effect a predetermined spacing of the particles. The device further includes an excitation waveguide configured to receive an excitation beam from a source to provide the excitation beam to the fluid channel, an excitation lens arranged to receive the excitation beam directed toward the fluid channel and focus the excitation beam to a predetermined width that is less than the predetermined spacing of the particles in the fluid channel to induce an interaction between the excitation beam and the particles resulting in a transmitted light, and a detection lens arranged relative to the transmitted light to guide the transmitted light along a plurality of paths. Further features of the device include at least one scattered waveguide to receive light scattered by the particles, the at least one scattered light waveguide further configured to interface with a detector, an axial light loss waveguide to receive light guided by the detection lens along at least one of the plurality of paths and not received by the at least one scattered light waveguide, the axial light loss waveguide further configured to interface with the detector.

In one aspect, the scattered light waveguide includes at least one forward scatter waveguide to receive light guided by the detection lens along at least one of the plurality of paths. In another aspect, the scattered light waveguide comprises at least one side scatter waveguide to receive light at a high scatter angle relative to the optical axis of the system and greater than the angles collected by the at least one forward scatter and axial light loss waveguides.

In one aspect, at least one surface of the excitation lens and the detection lens is an aspheric surface. In another aspect, the particles are biological molecules such as red blood cells, white blood cells, and platelets. In another aspect, the particles can be fluorescently labeled or unlabeled biological molecules, fluorescent particles, synthetic microparticles, polymer microspheres and/or magnetic microspheres. In yet another aspect a transverse cross-section of the fluid channel is rectangular and in another aspect, the waveguides are step-index waveguides including a first and second material, where the refractive index of the first material is greater than the refractive index of the second material.

In another aspect, the detector is configured to interface with a processor, the processor configured to receive the detection signal and determine characteristic features of each of the plurality of particles based on the detection signal.

In accordance with a third aspect of the present invention, a kit is provided for performing a point-of-care diagnostic. The kit includes a source of an excitation beam and a microfluidic device. The microfluidic device includes a fluid channel having a geometry configured to effect a predetermined spacing of the particles, an excitation waveguide configured to receive the excitation beam from the source to provide the excitation beam to the fluid channel, an excitation lens arranged to receive the excitation beam directed toward the fluid channel and focus the excitation beam to a predetermined width that is less than the predetermined spacing of the particles in the fluid channel to induce an interaction between the excitation beam and the particles resulting in a transmitted light, a detection lens arranged relative to the transmitted light to guide the transmitted light along a plurality of paths, at least one scattered light waveguide to receive light scattered by the particles, the at least one forward scatter waveguide further configured to interface with a detector, and an axial light loss waveguide to receive light guided by the detection lens along at least one of the plurality of paths and not received by the at least one scattered light waveguide, the axial light loss waveguide further configured to interface with the detector. The kit also includes a detector arranged to receive transmitted light from the at least one forward scatter waveguide and from the axial light loss waveguide and generate a detection signal based thereon, and a processor configured to receive the detection signal and determine characteristic features of each of the plurality of particles based on the detection signal.

In one aspect, the processor is configured to generate an output related to at least one diagnostic assay including a standard blood count, platelet and coagulation assay, a CD4+/CD8+ HIV diagnostic assay_ENREF_29, and a bead-based immunofluorescent assay.

In another aspect, the kit is configured for use in a clinical assay and/or a point of care assay. In yet another aspect, the excitation lens and the detection lens can have a surface defined by the following equation:

$$z(r) = \frac{cr^2}{1 + \sqrt{1 - (1+k)c^2 r^2}} + \sum_{i=4,6,8,...} A_i r^i;$$

where z(r) is a surface profile as a function of distance off an optical axis, r, of the at least one of the excitation lens and the detection lens surface curvature, c is an inverse of a spherical radius of curvature of the at least one of the excitation lens and the detection lens, k is a conic constant and $A_i$ are higher order aspheric terms.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 3A is an illustration that depicts cells (spheres) flowing through the small, rectangular channel focus into two streamlines (dotted lines). FIG. 3B shows a front view of cells centered within the cross-section of the channel, and a top view of cells spaced from one another along the flow direction by approximately 33 µm as measured with a high-speed camera. FIG. 3C shows an illustration of the propagation of the optical excitation beam along the x-axis and illumination of the channel in the y-z plane. FIG. 3D is a plot that illustrates why the interparticle spacing in FIG. 3B benefits from the beam intensity in the y-direction ($I_y$) being less than the sum of the interparticle spacing and the maximum diameter of particles of ~10 µm.

FIG. 4A is a schematic illustration of a cross-section of an optofluidic device in accordance with the present invention taken through the optical axis. FIG. 4B is a plot of the fractional power loss out of plane, as a function of the waveguide spacing, L.

FIG. 5A is a plot of transverse distance as a function of propagation length. FIG. 5B is a plot of the integrated intensity of the rays at the different detector surfaces as a function of beam cross-section.

FIG. 6A is a photograph of the cytometer in accordance with the present disclosure, which is a molded piece of COP bonded to another COP backing plate. FIG. 6B shows a reflectance image of an original master, faithfully reproducing the curved surfaces shown in FIG. 2. FIG. 6C is a plot of sag as a function of displacement from the optical axis. FIG. 6D is an image of the cytometer demonstrating the optical focusing performance.

FIG. 7A is a plot of forward scattering voltage as a function of time showing sample voltage signal for 10 µm bead scattering. FIG. 7B shows a pulse height histogram of the data from FIG. 7A plotted as frequency of peak vs. peak voltage. FIG. 7C is a plot of pulse width as a function of drive pressure. The correlation between cytometer and Coulter counts are shown in FIG. 7D for platelets (squares) and red blood cells (diamonds). FIG. 7E-7F are scattergrams of axial light loss vs. forward scatter voltage. FIG. 7E shows data for a platelet enriched plasma sample, while FIG. 7F shows data for a dilute whole blood sample.

FIG. 13A is a schematic drawing of the geometry of the example excitation and collimation lens, with aspheric constants.

FIG. 13B is an enlarged partial view of the schematic drawing of FIG. 13A as taken along the path 13B-13B.

FIG. 15A shows a typical darkfield system that collects scattered rays and blocks parent beam with dark stop. FIG. 15B shows an adaptation of this concept with optical waveguiding system. The incident beam is collimated using a lens structure and is captured using a collection waveguide instead of a beam stop while off-axis scattered rays are collected in a separate waveguide positioned next to the parent waveguide structure.

DETAILED DESCRIPTION OF THE INVENTION

The present invention is presented in several varying embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the system. One skilled in the relevant art will recognize, however, that the system and method may both be practiced without one or more of the specific details, or with other methods, components, materials, and so forth. In other instances, well-known structures, materials, or operations are not shown or described in detail to avoid obscuring aspects of the invention.

Figure 1:
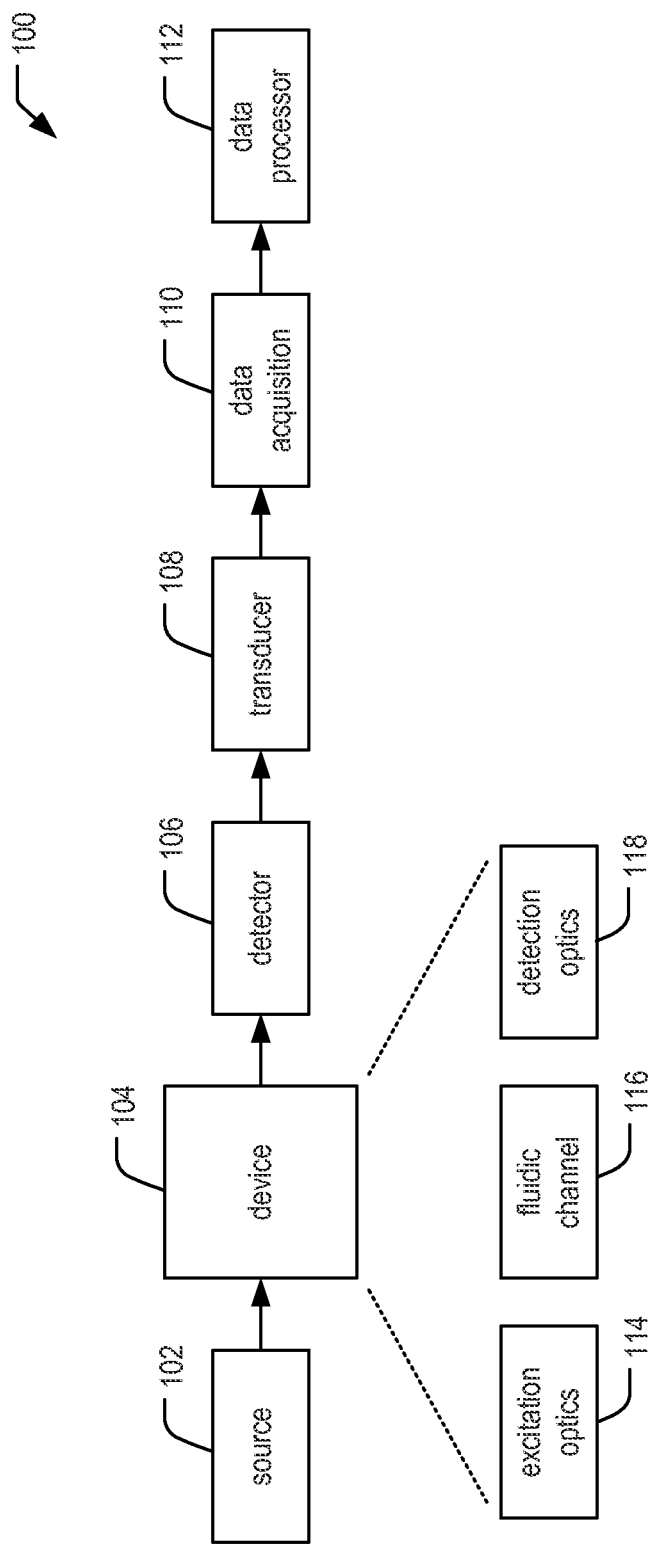
FIG. 1 is a block diagram showing the components of a system in accordance with the present invention including an emission source, an optofluidic device, a detector, a transducer, a data acquisition component, and a data processor.

Referring now FIG. 1, an integrated optofluidic system 100 is provided. In one example, system 100 may be used as a cytometer including a flow cell. As shown in FIG. 1, system 100 includes a number of components and subsystems. In example system 100 shown in FIG. 1, a source 102 delivers an excitation beam to a device 104. As will be detailed, the excitation beam is incident upon a flow cell incorporated into device 104 and is transmitted through device 104 by way of a number of components, such as excitation optics 114, at least one fluidic channel 116, and detection optics 118. In one aspect, the device 104 is a microfluidic device including fluidic channel 116. The excitation optics and detection optics, which can be either internal or external to the microfluidic device, can include lenses and waveguides.

The light is transmitted from device 104 to a detector 106. Examples of detectors include photomultiplier tubes and photodiode arrays. In one aspect, detector 106 can convert a transmitted light signal into a current, which can be passed to a transducer 108. In another aspect, transducer 108 can convert the current signal to a voltage signal. System 100 can further includes a data acquisition component 110 to receive and analyze the voltage signal and convert it to an electrical signal that can be processed by a data processor 112. In one aspect, data processor 112 can analyze the information from data acquisition component 110 to characterize a sample provided to device 104. For example, data processor 112 can determine a size distribution of or a composition of the particles.

System 100 can be used to analyze a variety of particles including labeled or unlabeled biological molecules, fluorescent particles, synthetic microparticles, polymer microspheres and magnetic microspheres. In one example, the particles are labeled with fluorescent molecules such biological molecules including proteins. The proteins are can be antibodies, oligonucleotides, polypeptide molecules, fluorescent proteins, avidin and its derivatives, and/or protein G and its derivatives. In another example, system 100 can be used to analyze a blood sample to determine a composition of red blood cells and platelets.

Figure 2:
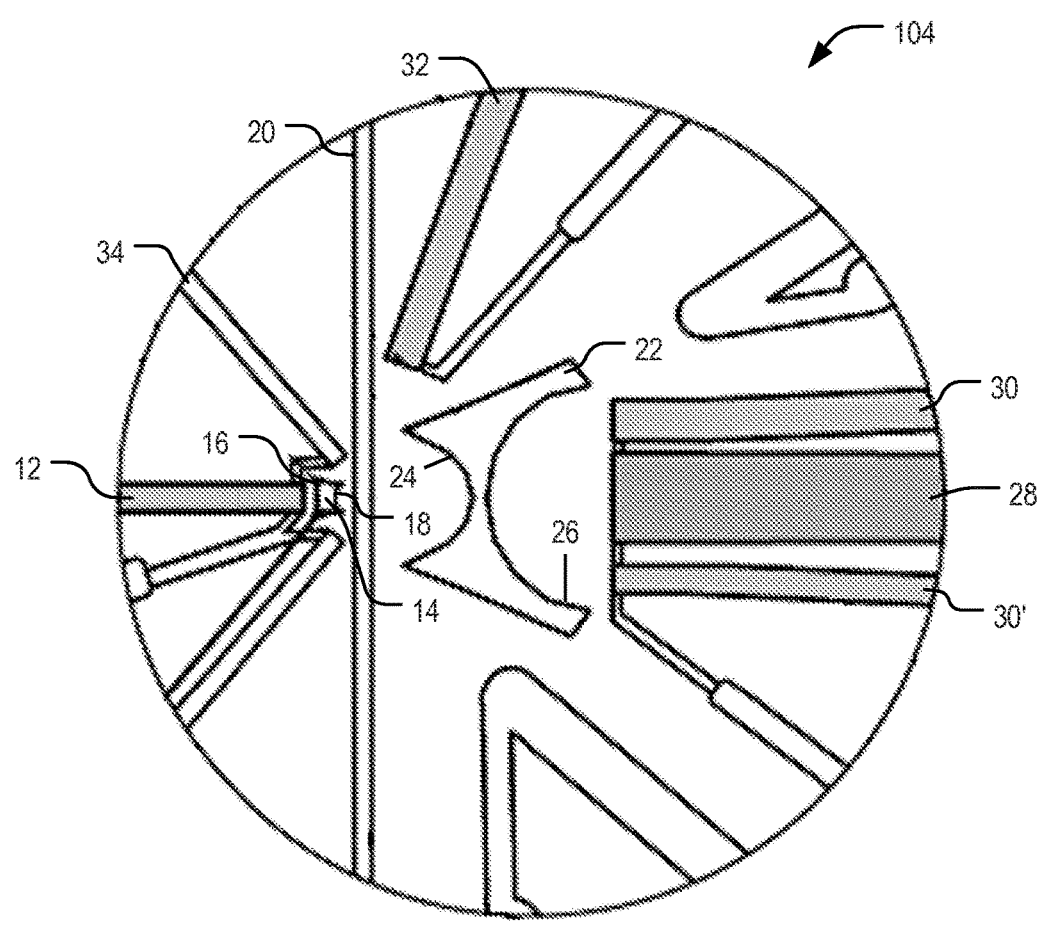
FIG. 2 a plan view of a subset of optical and fluidic components of the optofluidic device of FIG. 1 the design and layout of the waveguides and lenses for an embodiment of the present invention.

Referring to FIG. 2, an embodiment of device 104 is shown in further detail. In the present example, device 104 includes an excitation waveguide 12, which guides an excitation beam from a source (such as shown in FIG. 1) towards an excitation lens 14. Excitation lens 14 has a first surface 16 oriented toward excitation waveguide 12 and a second surface 18 opposing first surface 16. Surfaces 16, 18 can have a shape defined by an aspheric curve as defined generally by Eq. 1, which is discussed below. The purpose of the shape of surfaces 16, 18 is to guide and narrow the excitation beam from waveguide 12 toward a fluid channel 20.

Fluid channel 20 can contain particles from a sample provided to device 104. The geometry of channel 20 may be configured to spatially orient the particles with a predetermined interparticle spacing. In one aspect, the particle orientation is controlled with inertial focusing. One method to effect inertial focusing of the particles includes a fluidic channel with a diameter less than about 300 µm. In addition, the cross-section, such as a rectangular cross-section is selected to effect spatial orientation of the particles in the fluid channel. Preferably, the lens 14 can narrow the excitation beam to a width less than the interparticle spacing in channel 20. The interaction of the excitation beam with particles in channel 20 results in transmitted light, which can include forward scattered light and axial light (i.e., light transmitted through fluid channel 20 along the path of the incident excitation beam). A detection lens 22 is positioned relative to fluid channel 20 to receive a portion of the transmitted light. Lens 22 has a first surface 24 oriented toward fluid channel 20 and a second opposing surface 26. Analogous to lens 14, surfaces 24, 26 can have a shape defined by an aspheric curve as defined generally by Eq. 1. The purpose of the shape of surfaces 24, 26 is to guide the transmitted light from channel 22 toward an axial light loss waveguide 28 and forward scatter waveguides 30, 30'.

Waveguides 28, 30, 30' are configured to interface with a detector such as detector 106 of FIG. 1. Transmitted light in each of the waveguides 28, 30, 30' can be individually detected in order to characterize one or more aspects of the particles in channel 20. Furthermore, additional waveguides, such as side-scatter waveguide 32 or waveguide 34 to collect additional light transmitted or reflected from channel 20. In one aspect, side scatter waveguides 32, 34 are used to collect fluorescently scattered light. Side scatter waveguides 32, 34 may be configured to receive light incident at an angle of 80° and 135°, respectively. Thus, the side-scatter waveguides 32, 34 may be referred to as 80° side-scatter waveguides 32 and 135° side-scatter waveguides 34, respectively. In this regard, waveguides 32, 34 are used for wide angle scatter detection. However, side scatter waveguides can be oriented at any suitable angle such as between about 45 and about 180 degrees to the optical axis. In addition to lenses and waveguides, other components can be included in the design of device 104, such as fill channels and channels that act as optical baffles for the forward scatter waveguides. As described above, lens surfaces 16, 18, 24, 26 may be optimized to a general aspheric surface in the embodiment of the device shown in FIG. 2. Fit values to these surfaces are shown in Table 1.

Figure 3A:
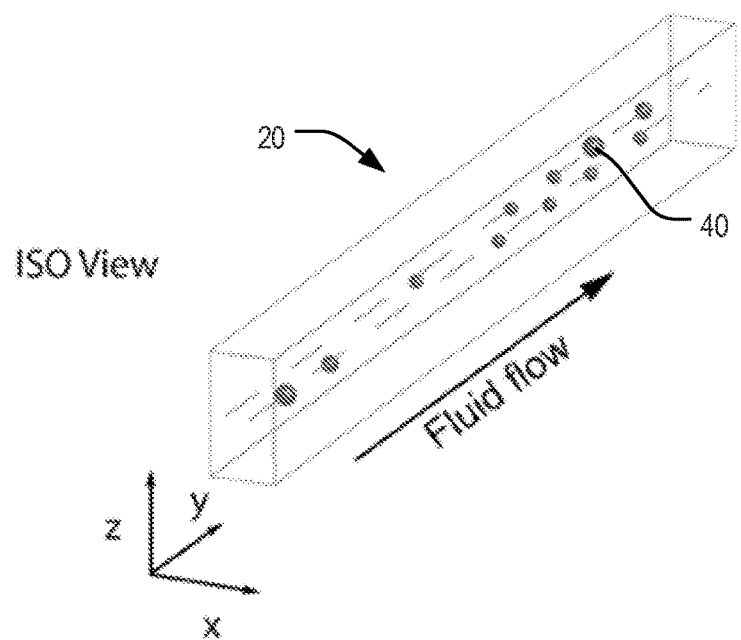
FIGS. 3A-3D are schematic illustrations that show an overview of flow cell design constraints.
Figure 3B:
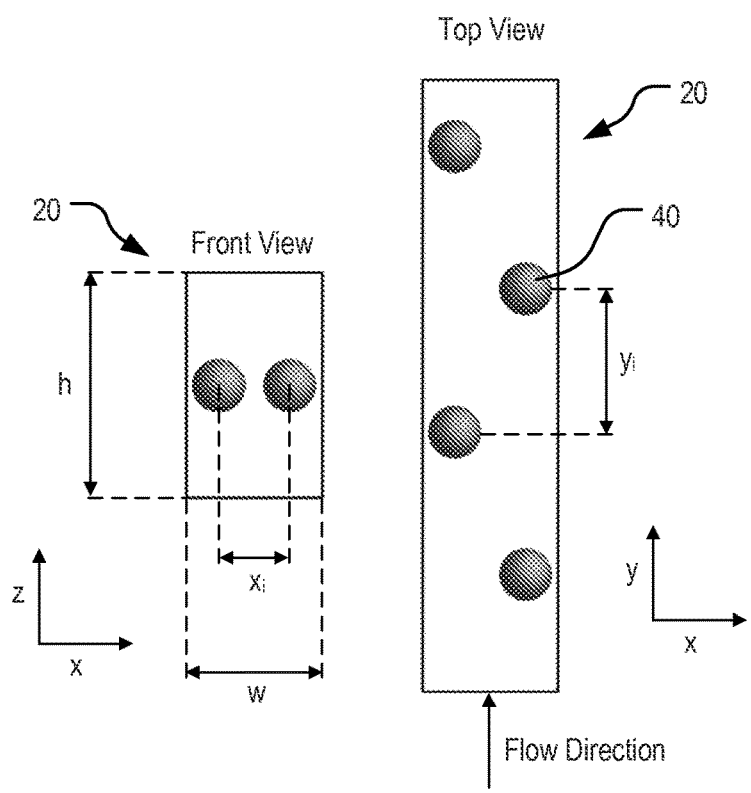
Figure 3C:
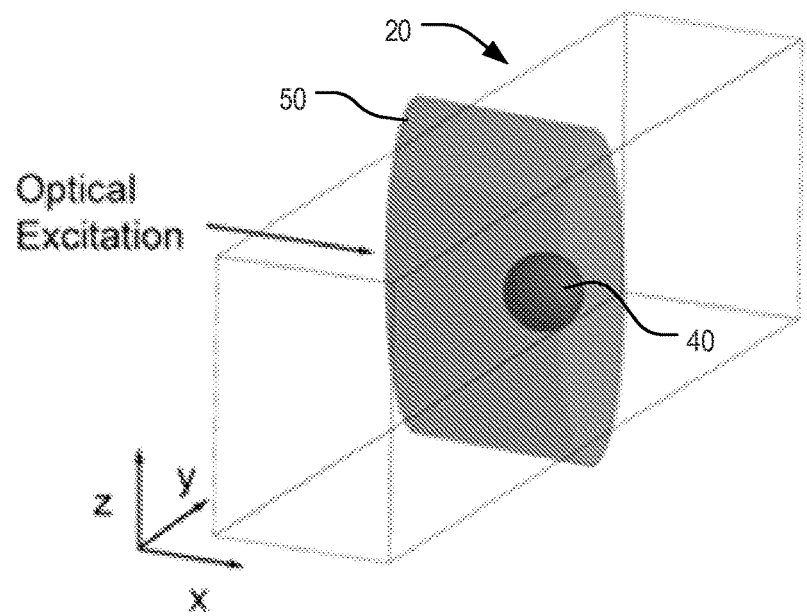
Figure 3D:
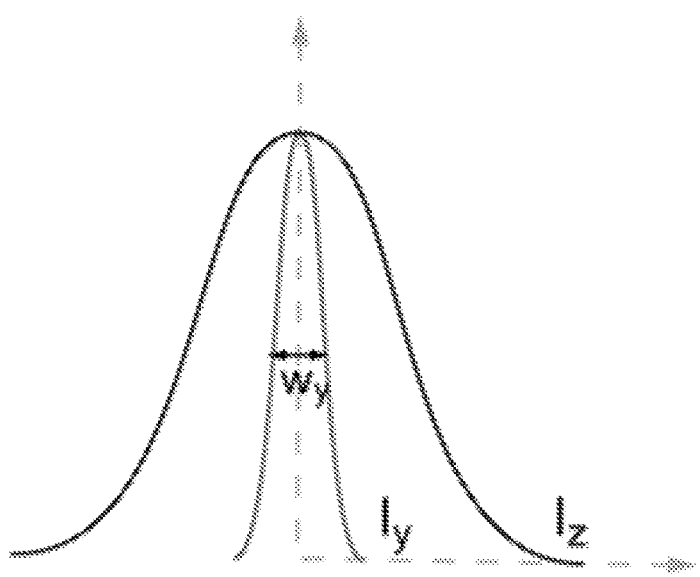

The flow cell employed can be a sheathless design that utilizes inertial focusing to spatially localize particles 40 (e.g., cells) within the fluid stream in channel 20. In one design, a rectangular geometry causes cells to focus along two positions within channel 20 cross-section as shown in FIG. 3A-3C. In order to accurately measure scattered light and quantitatively count particles 40, the width of the optical excitation beam formed by the waveguiding optics is preferably less than the interparticle spacing, $y_i$. In one example for particles 40 of up to 10 µm in diameter, the interparticle spacing, $y_i$, was measured to be 33 µm, setting the upper limit for the beam width at 23 µm (FIG. 3B). Also shown in FIG. 3B is the height, h, and width, w, of channel 20, as well the interparticle spacing, $x_i$ in the x direction (transverse) of channel 20.

In one aspect, for the detection of particles, it is preferable to create a device that can detect both scattering and axial light loss of cells. To achieve this, the incident laser beam can be separated from the light scattered by cells and particles traveling within the flowcell. In one embodiment, the present optical system is designed to: (i) focus from the output of the excitation waveguide, for example, to less than 23 µm in width; (ii) redirect the primary excitation light into a waveguide; and (iii) collect the scattered light into a separate waveguide with controlled contamination of the parent beam. In one method of implementing the aforementioned design, light is guided within a high refractive index polymer surrounded by a lower index cladding material. An example of a step-index waveguide design employs an optical-grade thermoset epoxy for the high index core, while a low-index cladding is a cycloolefin thermoplastic (COP). The COP cladding is the substrate of the device, which contains channels for the fluid flow cell, channels for the waveguiding epoxy, and air spaces that act as lenses for light.

The step-index waveguide design can include a variety of materials. Examples of materials that can make up the high-index core include: optical grade epoxies, engineered optical thermoplastics (e.g., COP, cycloolefin copolymer, polycarbonate, and polyacrylics), silane elastomers or hydrocarbon oils, including but not limited to hydrogenated terphenyls, aliphatic hydrocarbons and 1-bromonaphthalene. Examples of materials that can make up the low-index cladding include: glass, silicon, quartz or other crystalline materials (e.g., sapphire, diamond), and/or thermoplastics (e.g., COP, cycloolefin copolymer (COC), polycarbonate, and polyacrylics).

In another example of a device of the present invention, waveguides are formed by round waveguide inserted into a channel. The round waveguides can be made up of step index or gradient index optical fibers as described above. Furthermore, the waveguides, lenses, and optical systems in general can be positioned external to the device. In this example, the device includes one or more microfluidic channels and optionally the excitation or detection optics with the remaining optical components being external to (and configured to interface with) the device.

For a step-index waveguide, light propagates through the channels within a certain angular acceptance based on the difference between core and cladding index of refraction. In the example device described above, the optical-grade thermoset epoxy core material has an index of refraction of 1.542±0.003, while the COP cladding material has an index of refraction of 1.525±0.002. The high index core and low index cladding materials are preferably chosen to set the numerical aperture (NA) of the system to the desired value. For example, in the example device, the NA was set to 0.23 based on the choice of high and low index materials to allow for easy injection of external light into the system using fibers with a lower NA.

Figure 4A:
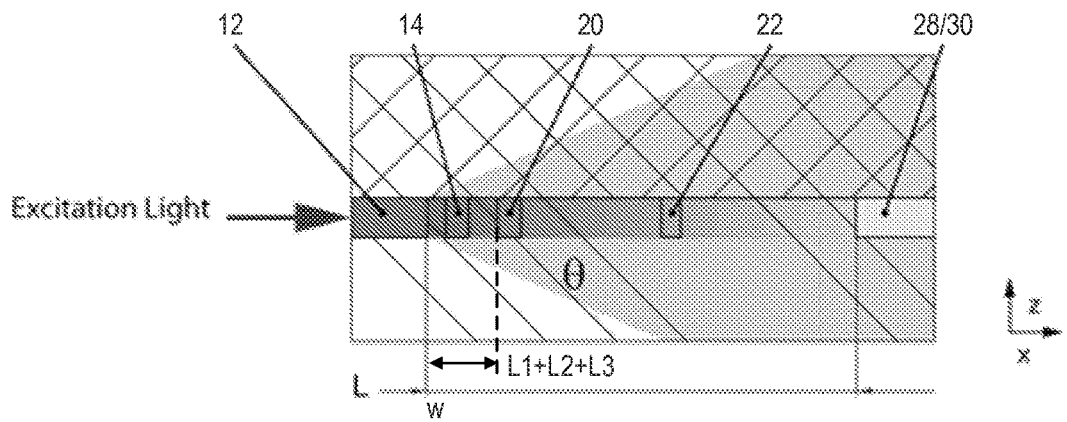
FIGS. 4A-4B provide an overview of waveguide dimensional constraints.
Figure 4B:
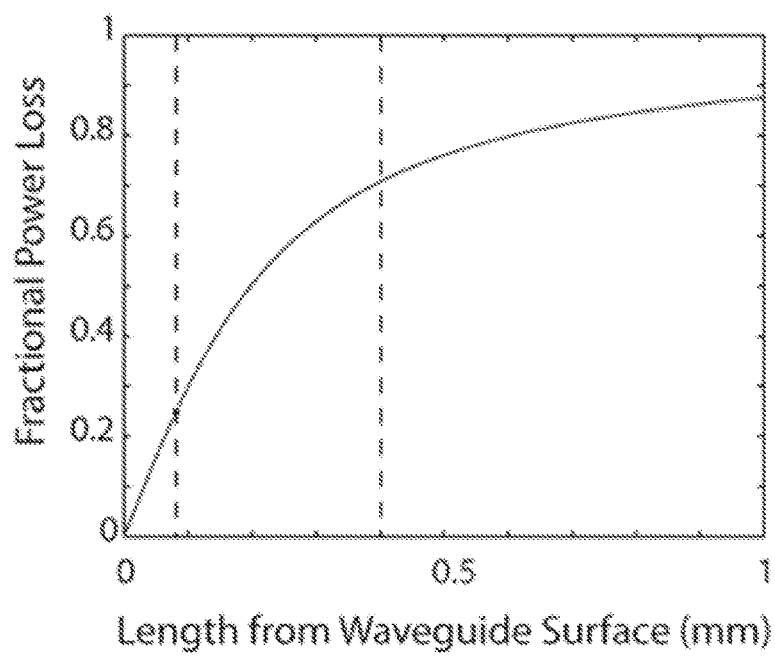

In some aspects, the step-index waveguide designs can exhibit loss of light out of plane at the end face of the waveguide. Light can exit the waveguide at an angle, θ, determined by the waveguide NA, as shown in FIG. 4A. This out of plane light is lost to the detection waveguide at a rate that is determined by the NA and the spacing between the excitation and collection waveguide faces. The loss as a function of distance, L, is shown in FIG. 4B. The two dashed lines represent the distance from the excitation waveguide to the center of the flow cell, and the distance between excitation and detection waveguides, respectively. One approach to minimize this loss involves the design of a system that minimizes the distance (L) between the waveguide faces, but still meets the aforementioned requirements.

In one implementation of the present invention, a design for the lenses that shape the optical beams was based on 2D and 3D raytrace simulations. Sequential raytrace simulations were performed at the laser wavelength, 657 nm, using the wavelength-specific index of refraction for the materials above. With the proper material parameters input into the model, the shape of the optical surfaces was optimized subject to a series of metrics. First, it was determined that the width of the beam may be preferably no larger than NA (e.g., 23 µm) at the center of the focus. Second, at least about 99.5% of the parent beam may preferably be collected by the detection waveguide to prevent contamination into the scattering waveguides. Third, the out of plane power loss for the excitation beam at the flow cell should, in some configurations or under some situations, not exceed about 30%. While these metrics were chosen in the design of one possible embodiment of the present invention, variations on these metrics as well as other metrics can be used based on the desired outcome.

In addition to these metrics, a set of constraints can be imposed based on the method selected for manufacturing the device. In the present example, thermal embossing was selected. Therefore, a first metric was that each surface of the different optical elements was preferably spaced by a minimum of about 25 µm to allow for molding of the COP device. A second metric was that any corners preferably have a radius of about 5 µm. A third metric was that all waveguide channels preferably are at least about 50 µm in diameter in order to couple to the core of the fibers used to interface with the device. These example optimization metrics and constraints were used to develop a merit function that was minimized during the raytrace simulations.

Figure 5A:
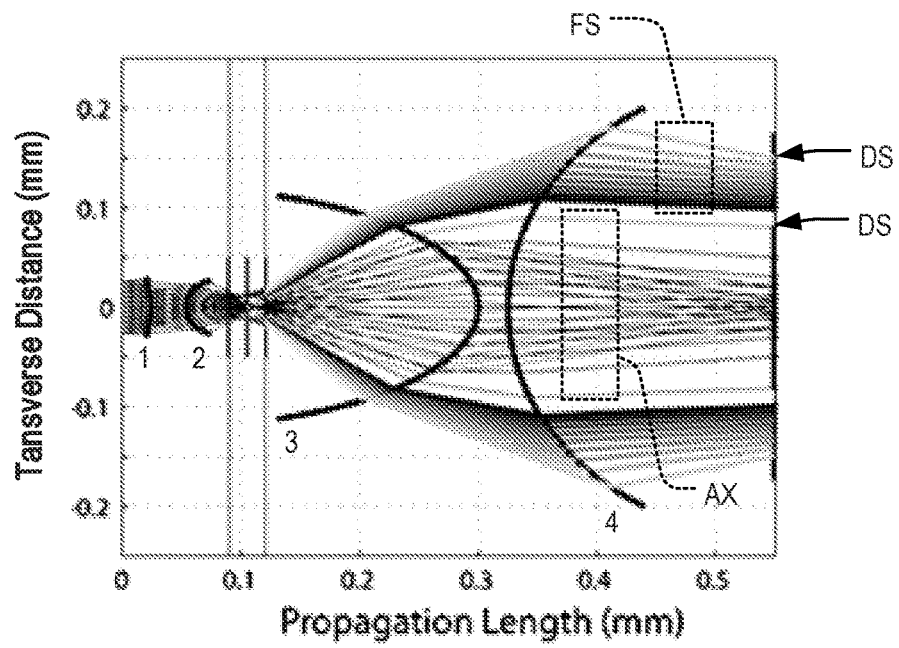
FIGS. 5A-5B show results of 2D raytrace simulations of the waveguide system.
Figure 5B:
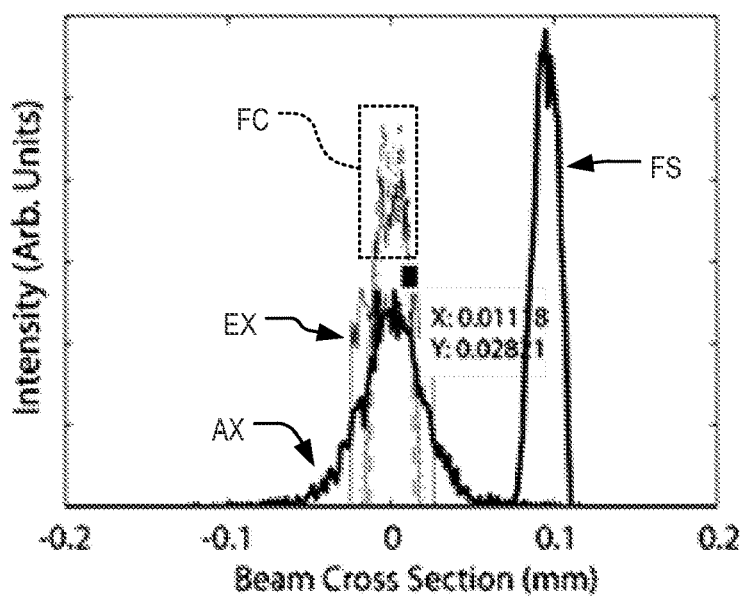

The results of raytrace simulations for an example device are shown in FIGS. 5A-5B. In FIG. 5A, the main system rays from the excitation fiber (x=0) are shown as thin lines (AX). At the center of the fluid channel (vertical lines near 0.1 mm), another set of rays representing scattered rays at 30-40° are also propagated (thick lines, FS). The lens surfaces optimized in the simulation are shown as curved thick lines (1-4), and detector surfaces (DS), where the optical field is sampled are shown as thick lines at ~0.55 mm. In FIG. 5B, thin line EX is at the excitation waveguide surface. The thin line, dotted line, and dashed line (FC, dashed box) represent the intensity of the beam in the middle, front, and back faces of the flow channel. Thick line AX and thick line FS show the intensity of the light at the detector surface for the primary rays and the scattered rays, respectively.

Based on these results, a design can be generated that meets the above requirements subject to production constraints. In one example implementation of the present invention, the design consisted of two lenses, one placed between the excitation waveguide and the flow cell channel, and one between the flow cell channel and the detection waveguides. Each lens surface was optimized to a general aspheric curve given by Eq. 1:

$$z(r) = \frac{cr^2}{1+\sqrt{1-(1+k)c^2r^2}} + \sum_{i=4,6,8,\ldots} A_i r^i; \qquad \text{(Eq. 1)}$$

where z(r) is the surface profile as a function of distance off the optical axis, r, surface curvature, c (the inverse of the spherical radius of curvature), and k is a conic constant. Higher order aspheric terms, $A_i$ can be fitted. However, in the present example, the use of higher order aspheric terms gave no improvement in predicted performance. Accordingly, the higher order aspheric terms were left out of the design. Based on the constraints of the tested configuration, optimized parameters for the example design are shown in Table 1.

TABLE 1

| Aspheric Surface | Radius (mm) | Conic Constant (mm) |
|---|---|---|
| 1 | 0.080 | −30.44 |
| 2 | 0.028 | −0.025 |
| 3 | 0.055 | −0.787 |
| 4 | 0.237 | −0.106 |

One example design of a darkfield optical cytometer is shown in FIGS. 2 and 5A-5B. This design includes waveguides for the excitation beam and a waveguide to collect the primary beam. The waveguide for collection of the primary beam is used to measure coupling efficiency of the system, DC laser power fluctuations, and axial light loss (ALL) measurements. Adjacent to the ALL waveguide are two forward scatter waveguides. Because of the NA of the example waveguide system (0.23), the 50 μm width of the multimode excitation beam, and the production constraints, design of a collection waveguide system that could collect forward scatter light at angles of less than 30° was not readily achievable. Typical flow cytometers measure forward scatter light at angles between 3-20° off axis of the excitation light beam. For cells and particles 1-15 μm in diameter, light is forward scattered, and forward scattering detection can be accomplished using, for example, simple photodiodes and modest laser powers (~10 mW). For the current example design, an approximately 50-fold signal reduction compared to a traditional forward scatter system was predicted, which was accommodated by the pulse detection electronics.

Another aspect of the present invention includes waveguide cytometer characterization. In one example, a cytometer was built and tested for baseline performance. FIGS. 6A-6D show basic characterization data for one device that was constructed. The fluid channel 20 had a rectangular cross section of 30 μm wide×55 μm tall and was 45 cm in length. All of the waveguide and lens features were produced with the same height as the fluid channel 20, and were placed 4 cm from the inlet of the device. The chosen length was sufficient to achieve stable focusing of cells and beads at flow rates of about 10 to about 40 μL/min. The SU-8 master was replicated with a rigid elastomer that was used to mold the features into blank COP slides. The COP slide with molded features was then thermally bonded to a flat COP slide with access holes for fluid input. When interfaced with tubing, the devices held up to about 3 bar of pressure, which was sufficient to flow saline buffer at an average flow rate of 17 μL/min/bar. The optical system was interfaced with bare optical fiber through the ends of the waveguides at the edge of the chip. This process allowed for coupling of light from a fiber pigtailed laser and directing of light from the detection waveguides into a set of photodiode or photomultiplier tube detectors.

Figure 6A:
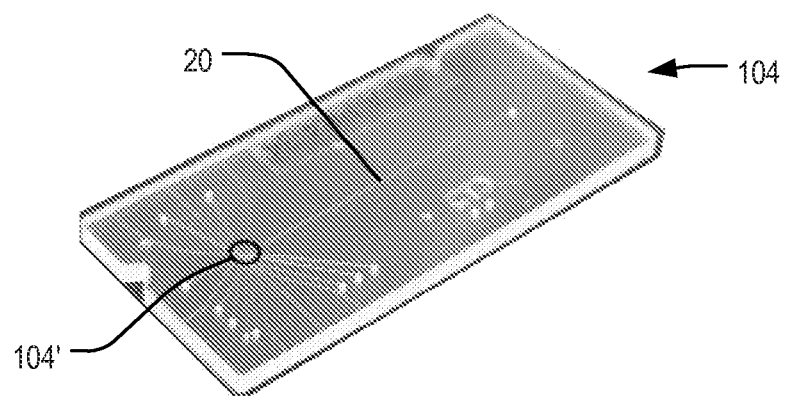
FIGS. 6A-6D provides an overview of cytometer characterization.
Figure 6B:
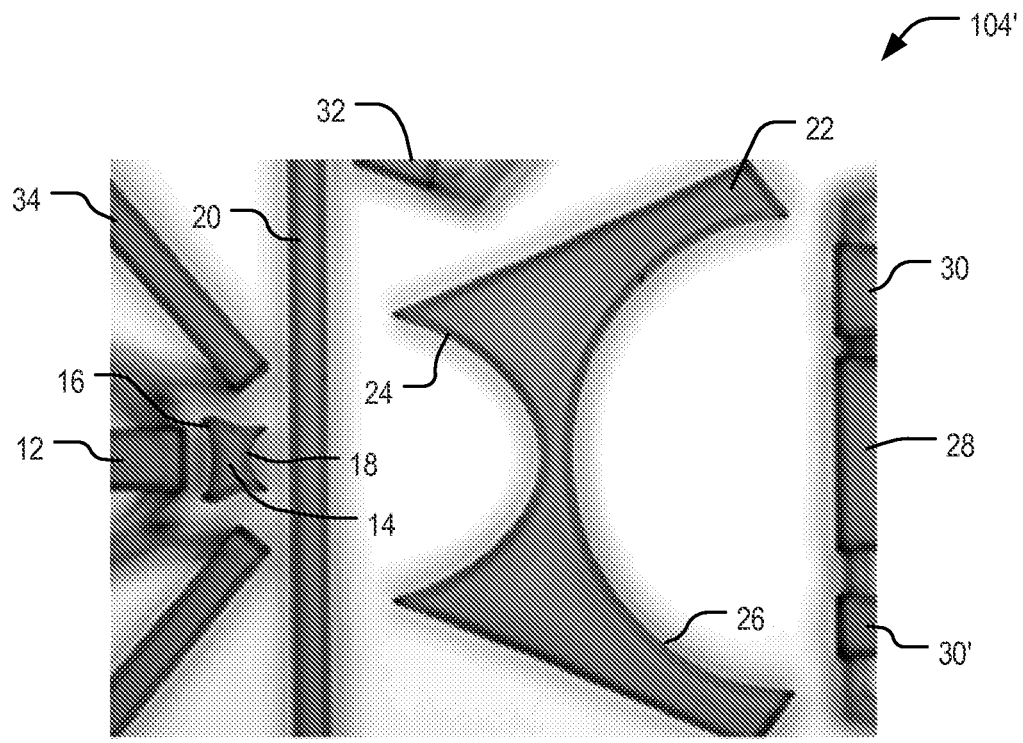
Figure 6C:
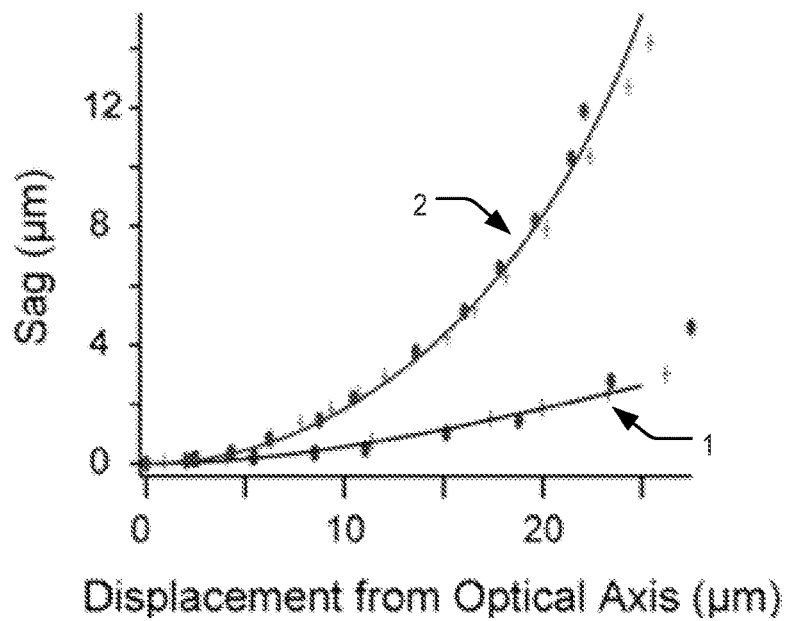
Figure 6D:
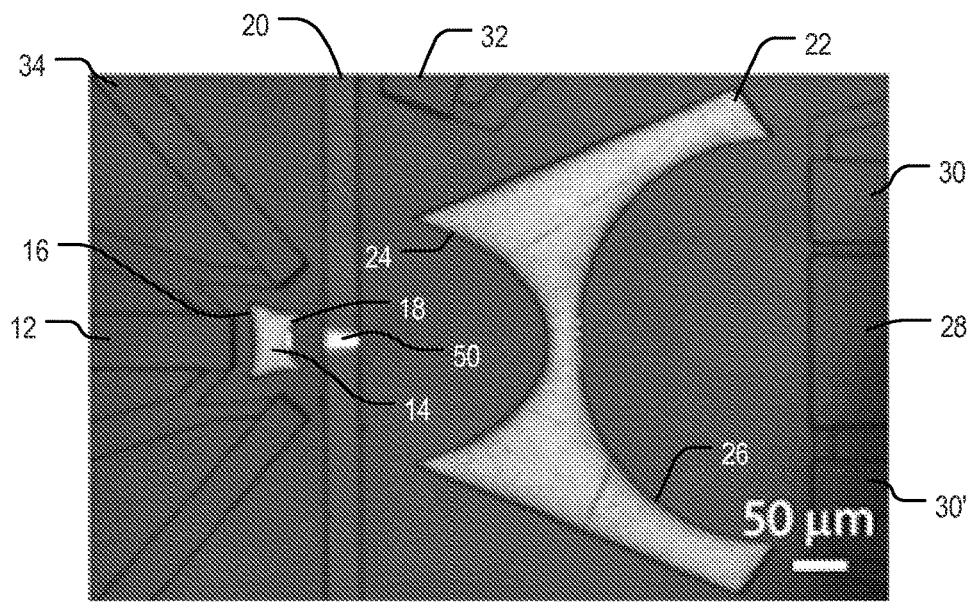

Specifically, FIG. 6A is a photograph of the device 104, which is a molded piece of COP bonded to another COP backing plate. Holes on the device face are for waveguide filling with epoxy and for access to the flow cell with stainless steel tubing. The COP device is molded from an elastomeric copy of an SU-8 master. FIG. 6A further shows fluid channel 20 and detail 104'. FIG. 6B shows a reflectance image of the original master for device 104 showing detail 104'. This master faithfully reproduced the curved surfaces shown in FIG. 2. FIG. 6C is a plot of sag as a function of displacement from the optical axis. The plot shows a comparison of the feature edges in FIG. 6B with design shapes for the excitation lens. The design curves for aspheric surfaces 1 and 2 are shown as solid lines. The measured sag for two different production masters is shown with crosses and ovals, respectively. FIG. 6D is an image of the device 104 showing detail 104' demonstrating the optical focusing performance. The fluid channel is filled with a fluorescent dye, and the waveguides are filled with optical epoxy. When light is launched through a fiber into the excitation waveguide, it focuses the excitation beam to a width of 14.8±0.8 μm at the center of the channel, which is indicated as focused beam 50. The beam width variation across the width of the fluid channel is ±4 μm from left to right. It can be seen from FIG. 6D that lenses 14, 22 are illuminated by light from the excitation beam.

The optical performance of the completed chip can be tested. To validate the example optical system, a red fluorescent dye was pumped through the optical channel and excited by the 657 nm laser source. The chip was imaged with a standard microscope equipped with excitation blocking filters and the beam width was measured at the center as well as front and back faces of the flow cell. From three different cytometers, the beam width measured was 14.8±0.8 μm, which was narrower than the predicted 21 μm from the ray trace model. In addition to static fluorescence images of the beam width, the light collection into the different detection channels was measured. A summary of the average coupling losses into different channels for three different assembled cytometers is given in Table 2.

TABLE 2

| Optical Coupling | Measured Coupling (dB) |
|---|---|
| Excitation - Axial light loss waveguide | −19.4 ± 1.9 |
| Excitation - Forward scatter waveguide 1 | −43.9 ± 1.2 |
| Excitation - Forward scatter waveguide 2 | −44.5 ± 0.9 |

With respect to losses for the axial light loss channel, coupling losses due to fiber-fiber coupling, fiber-waveguide coupling and slab losses were estimated to be approximately −14 dB. This suggests that the remaining losses are due to scattering off the walls of the waveguides, at a level of −2.3 dB/cm. This number compares with Bliss et al, who measured a 2.2 dB/cm loss for PDMS waveguide system (Bliss, C. L., et al., *Lab on a Chip* 7, 1280-1287, 2007). Furthermore, both forward scatter channels were measured to be an additional 22 dB below the DC optical power in the ALL waveguide (a factor of ~0.006), confirming the placement of the waveguides with respect to the optical design in FIGS. 3A-3C.

Figure 7A:
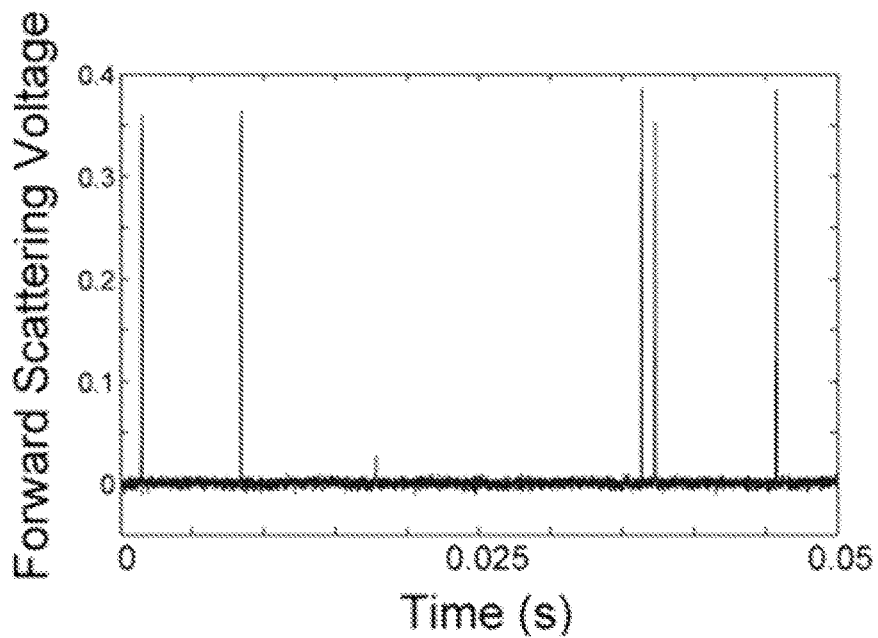
FIGS. 7A-7F are plots providing a summary of cytometer testing with beads or cells.
Figure 7B:
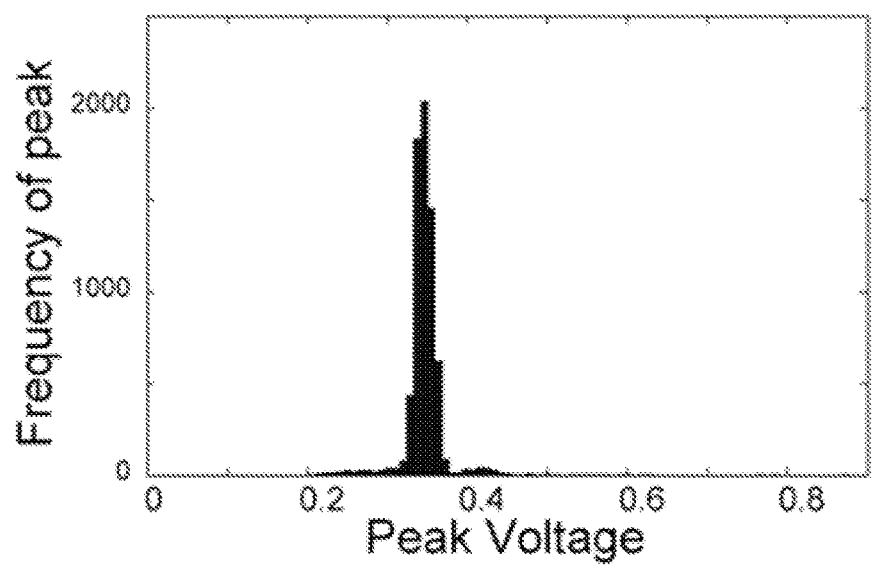
Figure 7C:
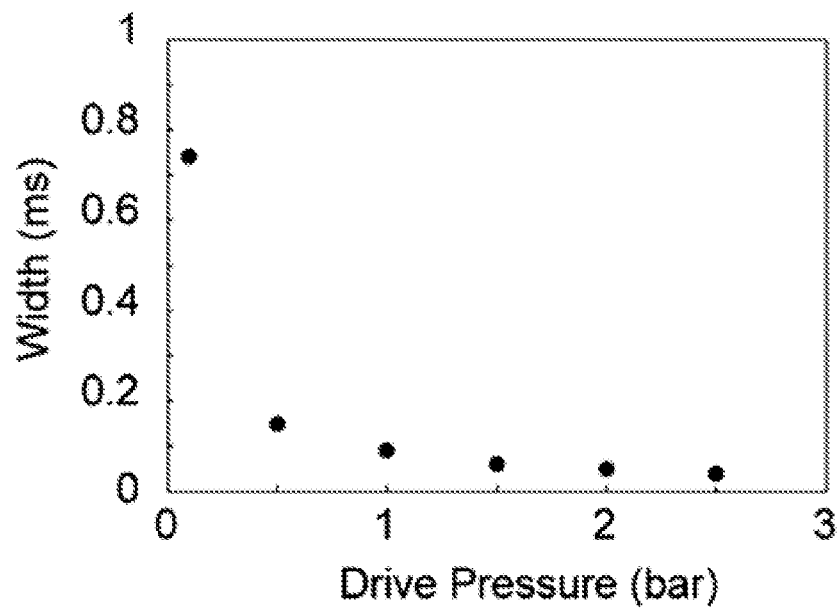

Once a validated design is achieved, the performance of the device as a functioning cytometer can be tested. An overview of the performance of an example device is shown in FIGS. 7A-7F. First different bead solutions were pumped through the flow cell and excited with the red fiber coupled diode laser. A sample trace of the scattered signals is shown in FIG. 7A. A peak detection algorithm built into a graphical programming platform was used to locate the location scattered peak height, position, and width of beads passing the optical detection system. Scatter height distributions were sufficient to discriminate between particles ranging in size from about 4.1 μm in diameter up to about 15 μm in diameter. To ensure that cells were focused within the fluid channel, both streak images of the cells were recorded and the peak width of the beads was measured. As shown in FIG. 7C the peak width decreased linearly from 0.5 to 2.5 bar. Pulse width was analyzed from 0.1 to 2.5 bar drive pressure. At 0.5 bar and above, the pulse width decreases linearly with drive pressure. The concentration of 6 μm, 10 μm, and 15 μm beads was measured over three orders of magnitude and the concentration was compared with a Coulter counter. For beads (triangles), the correlation between cytometer counts and the Coulter was 0.94 ($R^2$=0.998). Below 0.5 bar, the peak width lengthened, the peak height distribution broadened, and position within the channel randomized, suggesting that the inertial hydrodynamic forces were not sufficient to localize particles. These observations were confirmed with streak images and high-speed video. All additional experiments for analysis of the example device were driven with 2 bar pressure corresponding to 34 μL/min flow rate.

The ability of a cytometer to quantitatively count and discriminate particles over a range of concentrations can also be determined. Referring once more the example device, the concentration of 6 μm beads was measured over two logs of concentration (~40-4000 beads/μl). For these experiments data was collected over 3-5 minutes and counts derived from the scattergrams were compared with counts measured on a Coulter counter. Counts for three different concentrations measured in triplicate were linearly correlated with Coulter measurements with a slope of 0.94 ($R^2$=0.998).

Figure 7D:
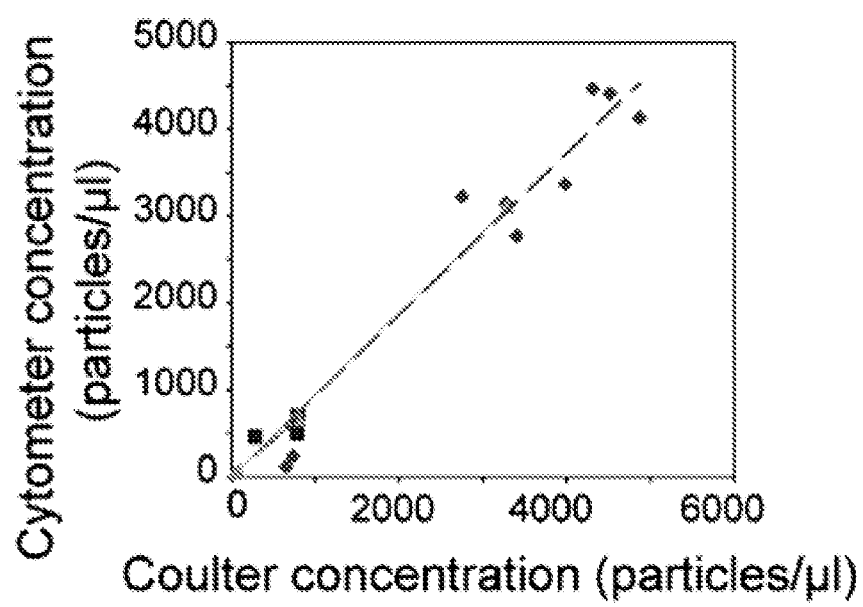
Figure 7E:
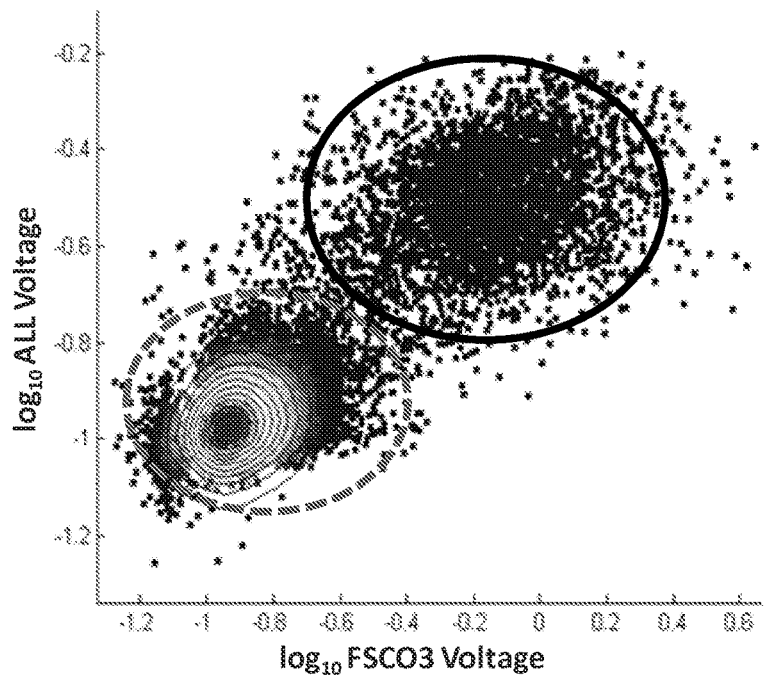
Figure 7F:
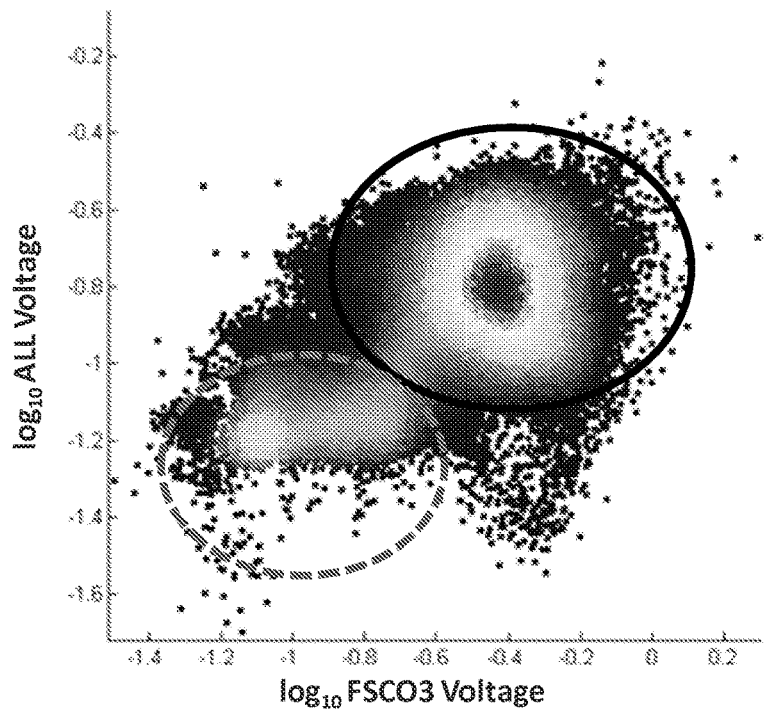

The present invention, in some embodiments, is useful for clinical diagnostics, such as the detection and characterization of cells. Therefore, the ability of an example device with integrated optics to measure a set of diluted whole blood samples was tested. In one aspect, the present invention can preferably discriminate between platelets and red blood cells and quantitatively measure each with about a 10% error or less. To test the ability of the example device to detect platelets, a platelet-enriched sample was measured as depicted in FIG. 7E. When plotted on a log scale, scatter from platelets (dashed grey oval) can be effectively discriminated from contaminating red cells (solid black oval). Dilute whole blood was also measured in order to test the ability of the example device to quantitatively detect and count red blood cells and platelets. FIG. 7F shows a representative scattergram for measurements of five samples (one in triplicate). FIG. 7D shows events counted in the platelet region and the red blood cell region compared with Coulter measurements. Gates for red blood cell counts (solid black oval) and platelet counts (dashed grey oval) are indicated. The red blood cells exhibited a correlation of 0.93 ($R^2$=0.926), while the platelet counts had a correlation of 0.82 ($R^2$=0.646). These data demonstrate the ability of a device such as the example inertial focusing cytometer with integrated optical elements to discriminate and enumerate cells relevant to routine clinical diagnostics.

EXAMPLES

One example of the design, construction and characterization of an optofluidic device begins with the identification of a suitable optical design. Ray tracing simulations were run on code written for a numerical computing environment and on optical and illumination design software. For waveguide propagation, non-sequential raytracing was performed in an optical and illumination design software with >100 k rays using individual rays or a planar source the size of the input coupling fiber (50 μm diameter core, NA=0.22). Detectors were placed at positions corresponding to the collection waveguides or along waveguides 1 mm in length beyond detection waveguide endfaces. Numerical computing environment simulations were sequential raytrace simulations carried out for 2D propagation of 5000-10000 rays. Sources originated at the end face of the excitation waveguide and rays were propagated to detectors at the faces of the detection waveguides. Optimization of lens surfaces was performed in both the optical and illumination design software and the numerical computing environment and gave similar results. Optimization for the excitation lens was performed by minimizing the beam width at the center of the fluid channel subject to geometrical constraints based on production methods. For the scattering collection lens, optimization proceeded by minimizing a merit function that sought to collimate the excitation beam, maximize intensity, and minimize width at the detection plane. Detection waveguides were placed such that the excitation beam would be rejected by a ratio of 1000:1 based on the raytrace simulation. In order to minimize overall device size, the detection waveguides were curved to spatially separate the different channels. Arc length of the waveguide curves was chosen to minimize bend loss. The final optimized geometry was input into a 3D computer aided drafting design software model for production as described below.

A next step of the example process involved production of the microfluidic device. Microfluidic devices were produced using a modified version of standard soft lithography. First, high resolution chrome masks were generated based on the optimized geometry, details of which are given in the Appendix. Three layers of thicknesses of 15, 55, and 70 μm were photolithographically patterned using MicroChem photoresist SU8 permanent epoxy resin on bare silicon wafers in order to make the negative masters. All fluid channels and waveguides were at a height of 55 μm, fill channels for the waveguides were made 15 μm, and interfaces for the external coupling fibers were made 70 μm. SU-8 masters were replicated in a cycloolefin copolymer using a soft-embossing process (Carvalho, B. L., et al., *Abstracts of Papers of the American Chemical Society*, 221, U103, 2001). COP chips were thermally bonded to a clear COP backing that had access holes for fluid filling. Waveguides were filled with an optical grade epoxy mixed and then degassed by centrifugation at 16000×g for 3 min. Once filled with epoxy, thin optical fibers connectorized on one end with a standard SMA-905 connector were cleaved and inserted into the edge of the chips. Fluid connections were made by gluing stainless steel tubing into access holes of COP backing.

Figure 8:
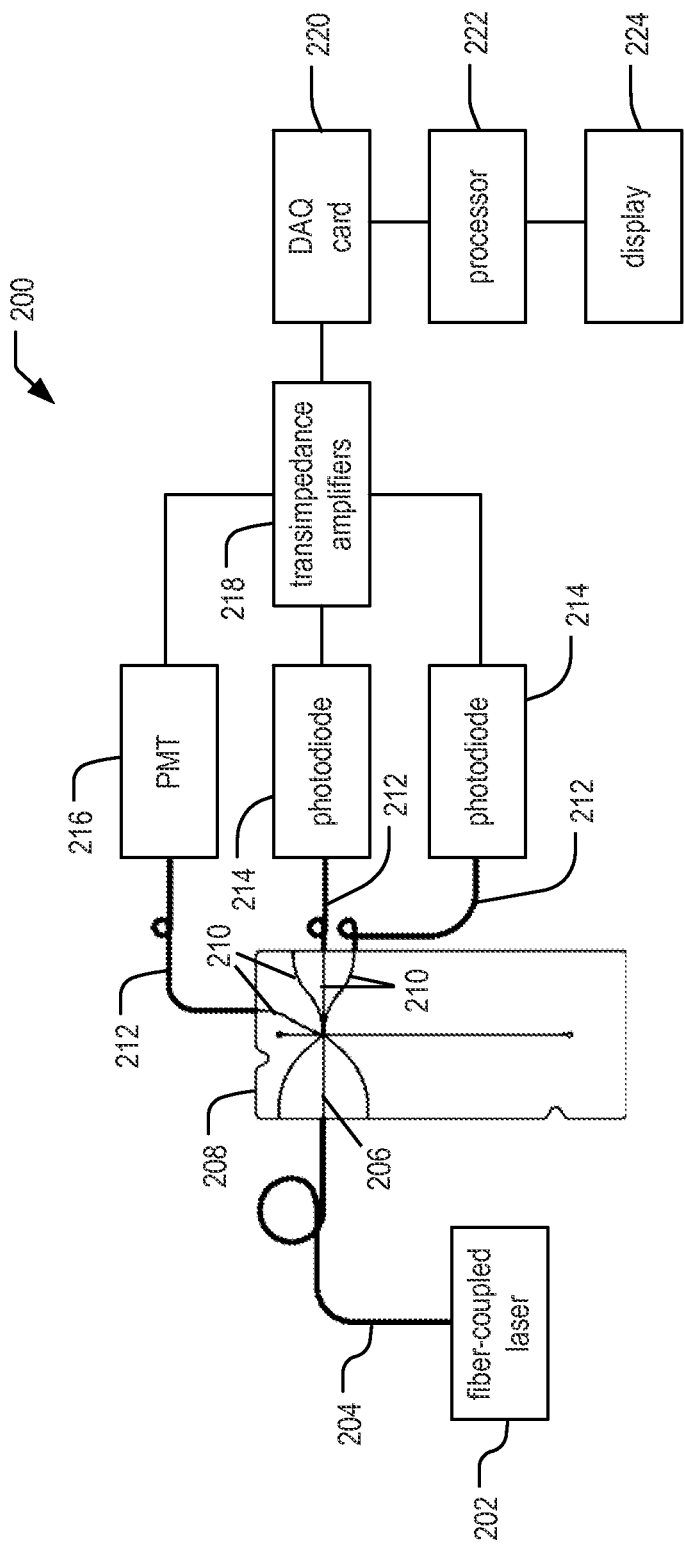
FIG. 8 is a schematic diagram of a system in accordance with the present invention.

Following production of the example device, a testing setup was assembled. A system 200 that was used in such tests is shown in FIG. 8. To create the system 200, a laser 202 was coupled through fibers 204 and interfaced to an excitation waveguide 206 of an integrated cytometer chip 208. Detection waveguides 210 were bonded to fibers 212 that were fed to either photodiodes 214 or photomultiplier tubes 216. Current detected from these chips 214, 216 was converted to voltage with a transimpedance amplifier 218 with baseline restore circuitry. The AC voltage was sampled by a DAQ card 220 controlled by a processor 222 using software written with a graphical programming platform.

More particularly, the fiber 204 glued to the excitation waveguide 206 of the cytometer 208 was connected to a 60 mW fiber coupled laser diode 202. Fibers 212 coupled to detection waveguides 210 were connected to either photodiodes 214 (axial light loss and forward scattering waveguides) or photomultiplier tubes 216 (side scatter).

Current from the photodetectors 214, 216 was converted to voltage with the transimpedance amplifier 218 with analog baseline restore capability, such as described in _ENREF_35Snow, C., *Cytometry A*, 57, 63-69, 2004, which is incorporated herein by reference in its entirety. These voltages were digitized at 100-250 kHz with the DAQ card 220 and read into the processor 222. In particular, the processor 222 processed the data streams using a peak detection algorithm in a graphical programming platform to calculate peak statistics (height, width, and area). The peak data was then processed and displayed through a report generator or display 224 using a numerical computing environment or a software package for analyzing flow cytometry data.

Experiments were carried out with polystyrene beads or processed whole blood samples. Whole blood was obtained and was processed according to BSL-2 safety procedures. To prevent settling, beads and cells were diluted in isotonic density matched buffer containing phosphate buffered saline and Histodenz™ nonionic density gradient medium. Samples were prepared at concentrations ranging from 10-5000 particles/µl and were flowed through the cytometer using a syringe pump or through a pneumatic driven source at rates between 1.2-40 µl/min. The density matched buffer flowed through the system at an average rate of 12±0.5 µl/min/bar drive pressure. Each experiment was run for three minutes and the sample outflow was collected and measured on a Coulter counter.

Thus, the present invention relates to the design, construction, characterization, and use of an optofluidic device. Embodiments of the present invention contribute to the design of a compact, easily manufactured, optical cytometer for cell counting. Inertial flow focusing can use minimal sample processing and a single pump for operation. Optical particle detection and characterization enables the use of a range of inexpensive optical sources and detectors (see, for example, Morgensen, K. B., et al., *Electrophoresis*, 30, S92-100, 2009; Myers, F. B., et al., *Lab on a Chip*, 8, 2015-2031, 2008; Habbersett, R. C., et al., *Cytometry A*, 71, 809-817, 2007) and the ability to carry out a wide range of assays including fluorescence.

In one aspect, the present invention does not need to rely on electrical impedance methods. While electrical impedance methods are attractive due to their small size and reduced system complexity, impedance based methods can be limited in assay menus for a generalized clinical measurement platform. To extend the simplicity of the inertial focusing chip, it can be preferable to decrease the complexity and the size of the optical system by incorporating optical elements within the microfluidic chip that contains the flow cell. Optics may be fixed in space by the manufacturing process and do not necessitate external adjustment over time to maintain alignment. This is an advantage for compact portable instrumentation that is subject to rugged environments or handling. Improvements to the design can be implemented in order to collect fluorescence and high angle scattering measurements from cells. These improvements can enable white blood cell counts, immunoassays and cellular phenotyping. Once incorporated, the present invention can enable compact point of care measurements for a wide range of clinical assays including standard blood counts, platelet and coagulation assays, CD4+/CD8+ HIV diagnostics_ENREF_29, and bead-based immunofluorescent assays.

In one embodiment, the present invention provides a microfluidic chip that combines integrated optics with inertial microfluidics for scatter detection and discrimination of particles. Inertial focusing gives rise to particle ordering which places strict technical requirements on the optical system design in order to detect single particles within an optical interrogation region. In one example, an optical system was designed that was capable of focusing a large multi-mode optical beam down to less than 20 µm. The combination of the relatively large numerical aperture of the excitation waveguide and width or mode density of the waveguide system can result in a number of design challenges. However, despite these challenges in achieving a focused beam, the achieved beam width was measured to be narrower than predicted. This difference can be attributed to slight rounding of the excitation lens features near the corners of the lens closest to the waveguide surface. Simulations of the light lost through this rounding predict a loss of approximately 20%, which was not detrimental to scattering measurements for beads and cells. The reduction in beam width, in one aspect, helped to reduce coincident events and to detect cells at high particle concentrations.

The present invention can further be used for the detection of scattering of platelets and red blood cells. In one example, scattering was determined as a benchmark for the range of measurements made in a clinical cytometer. Red cells typically occur in the blood at extremely high concentrations (~40-45% volume fraction or ~$4 \times 10^6$ cells/µl). For compact, point of care cytometry, minimizing fluid volumes is desirable. In one aspect, the present invention can measure red blood cells with a single 1000-fold dilution with buffer, approximately an order of magnitude less fluid than with a standard sheath-flow cytometer or Coulter measurement. Inertial focusing minimized coincident events allowing direct counts in such a highly concentrated sample.

The ability to focus platelets within a flow cell is not readily achieved due to their small size. One advantage of a present integrated cytometer design is that the excitation light fills the entire channel from top to bottom, and thus platelets are illuminated regardless of position within the flow cell. Platelets are challenging to measure optically due to small scattering cross sections. For this reason, observed correlations in platelet measurements were lower when compared to Coulter counts, but acceptable given the optical losses in the current system. It is anticipated that the optical design can be improved to collect scattered light at angles closer to the incident beam. In one aspect, this can be accomplished through adjustment of the collection lens to properly collimate the divergent multimode beam into a narrower collection waveguide closer to the flow cell. Moving the collection optics closer to the flow cell can increase the collected solid angle of scattering. Because scattered light for cells is highly forward directed, this should allow for an increase in the signal to noise ratio for platelet detection and improve enumeration of platelets.

In another embodiment of the current invention, the detection waveguides are patterned in such a way to exclude any detection lenses. In this embodiment, the numerical aperture of the axial detection waveguide is chosen to collect all the axial light based on the numerical aperture of the excitation lens system, which is determined by a combination of excitation waveguide size, acceptance angle, and focused spot size within the channel. In addition to the axial detection waveguide, a series of waveguides are placed to collect scattered light. The angles of acceptance in these waveguides are determined by their geometric orientation with respect to the fluid channel, the excitation light field, the maximum acceptance angle of the step-index waveguide, and the waveguide size.

The present invention can also include other features that improve darkfield detection performance. Such features include microfluidic channels that contain absorbing dyes that function to absorb or collect stray light. These absorbing channels act as optical baffles that limit the functioning aperture of the darkfield system. In addition to baffles, the waveguides can contain bends or curves that guide the light to different optical detectors. The radius of curvature of these bends is maximized to minimize light lost in the total internal reflection along the step index waveguide boundary.

In another example, an integrated cytometry module (ICM) for use within a Point of Care (POC) testing platform was designed, built and tested. In one aspect, the compact optical flow cytometry device was configured to measure the major components of blood as part of routine clinical diagnostics. Accordingly, the cytometer was designed to measure the optical scattering of red blood cells (RBCs), platelets (PLTs), and white blood cells (WBCs) at a set of defined angles with respect to an excitation light source. In addition to light scatter, the cytometer was designed to measure fluorescence of cells and particles for immunophenotyping and bead-based immunoassays, respectively.

The complete blood count (CBC) with differential (DIFF) may provide a broad diagnostic of a patient's health status and as such is one of the most widely ordered laboratory tests in clinical medicine. The CBC may provide information about oxygen carrying capacity through RBC measurements (number, hemoglobin, and hematocrit), immune function through WBC measurements (cell counts with subpopulation counting), and hemostasis through PLT counts. These measurements may be useful to clinical decision making and diagnosing anemia, certain cancers, infection, hemorrhagic states, allergies, and immunodeficiencies. A summary of the absolute cell counts for adult males in a CBC is presented in Table 3. These measurements may form the basis for systems requirements in the POC CBC analyzer (i.e., a device according to the present disclosure).

TABLE 3

| Absolute Cells Counts | Mean | 95% Range | ATE Limit (CLIA '88) | Suggested ATE $(10^6/ml)^4$ |
|---|---|---|---|---|
| Red Blood cells $(10^9/ml)$ | 5.5 | 4.9-6.2 | ±6% | |
| Platelets $(10^6/ml)$ | 285 | 147-422 | ±25% | |
| Total Leukocytes $(10^6/ml)$ | 6.7 | 4.4-8.2 | ±15% | |
| Lymphocytes $(10^6/ml)$ | 2 | 0.9-3.2 | | 0.2 |
| Monocytes $(10^6/ml)$ | 0.37 | 0.12-0.62 | | 0.2 |
| Neutrophils $(10^6/ml)$ | 4.01 | 1.31-6.71 | | 0.4 |
| Eosinophils $(10^6/ml)$ | 0.13 | 0.00-0.30 | | 0.2 |
| Basophils $(10^6/ml)$ | 0.05 | 0.01-0.09 | | 0.2 |

Figure 9:
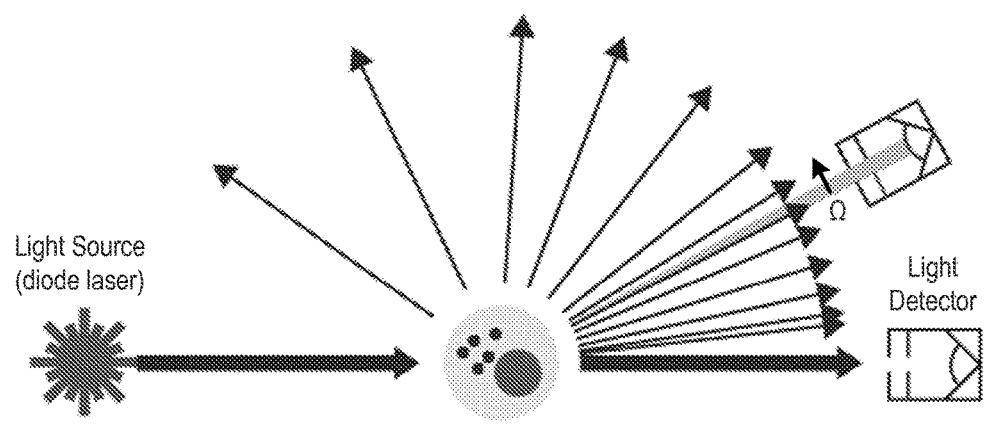
FIG. 9 is a schematic of optical scattering in flow cytometry. Laser light is focused onto a cell which scatters light into a wide range of angles (grey arrows). A fraction of this light with solid angle 52 is collected by the detectors for scatter measurement. The angular dependence of light scattering by cells can be described accurately using Mie theory.
Figure 10:
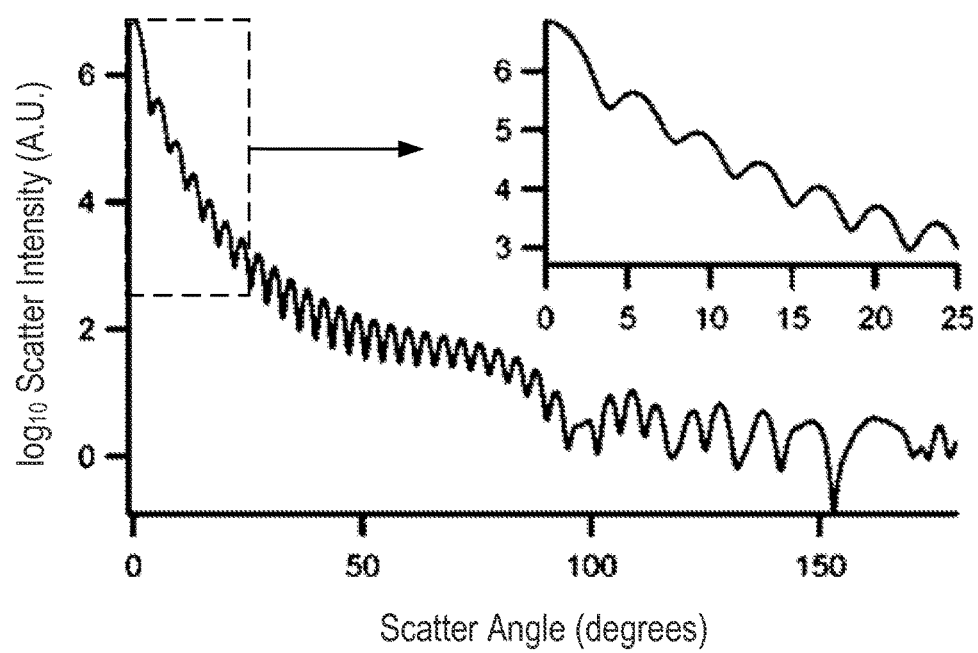
FIG. 10 is a plot of the relative scatter distribution into a range of angles for red blood cells.

To measure both cells in Table 3 and fluorescent immunoassays, a compact optical flow cytometry device was designed. This device was designed to be replaceable, but also reusable. Further, the device was designed to hold the tolerances described below, and fit within an about 12.7 cm (5 inches) long by about 7.62 cm (3 inches) wide by about 7.62 cm (3 inches) tall package. The fluid structures were microfluidic channels having a rectangular cross-sectional profile for the alignment of cells with respect to the one or more optical excitation sources. The one or more optical sources and scattering signals were directed to the fluidic circuit through a series of optical focusing elements (FIGS. 9 and 10). The detection angles were chosen to collect axial light-loss (ALL), forward scattering (FSC), side scattering signals (SSC), and backscattering or fluorescence, respectively. The detected light was used to discriminate and enumerate the cells in a CBC. Further, fluorescence signals were used for immunophenotyping of cells and for fluorescent bead-based immunoassays.

In order to make this device small, compact, and field serviceable, the cytometer for measuring particles was designed into a single monolithic structure containing both the optical system and fluid channels. With respect to the optical design of the device, the optical system in a cytometer measures particles that have been spatially aligned in a flow cell. Aspects of the optical system for measuring cells and particles may include focusing the excitation light with respect to the flow channel, focusing the excitation light to a sufficiently small spot size such that coincident events are less than the allowable total error (ATE) for the assay, and focusing the excitation light with sufficient uniformity to allow particle classification based on scattering distribution width. Further aspects of the optical system for measuring cells and particles may include a detection system capable of discriminating specific angles of optical scattering of light, a light source with sufficient power (intensity) to excite fluorescence and scatter light on detectors above the noise floor of the detectors, and detectors that can measure signals at specific wavelengths for scatter and fluorescence signals. Still other aspects of the optical system may include a light source of correct wavelength to excite fluorescence, and optical filters that can separate out different fluorescent signals from one another and from scattered excitation light.

Figure 11:
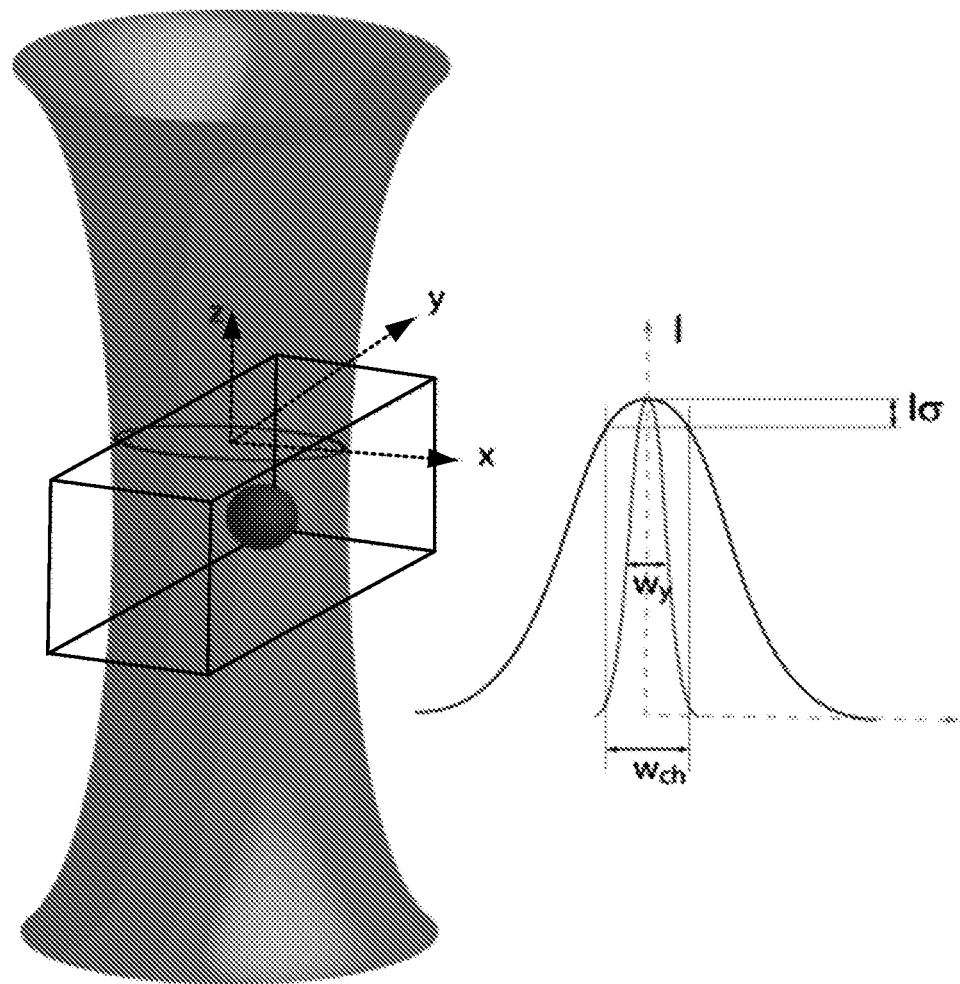
FIG. 11 is a schematic of the idealized shape of an excitation beam passing through a flow cell (left). The projection of the beam on the surface (right) with a beam width, $w_y$, in the y-z plane and variation in intensity, 1σ across the width of the flow channel, w, in the x-z plane.
Figure 12B:
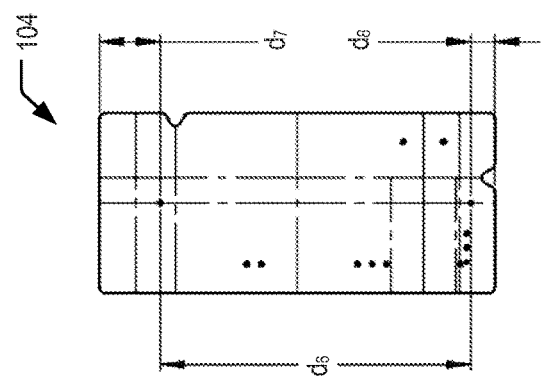
FIGS. 12A-12D are schematic drawings of an embodiment of a darkfield cytometer chip.
Figure 12D:
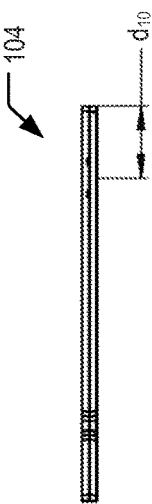
Figure 12A:
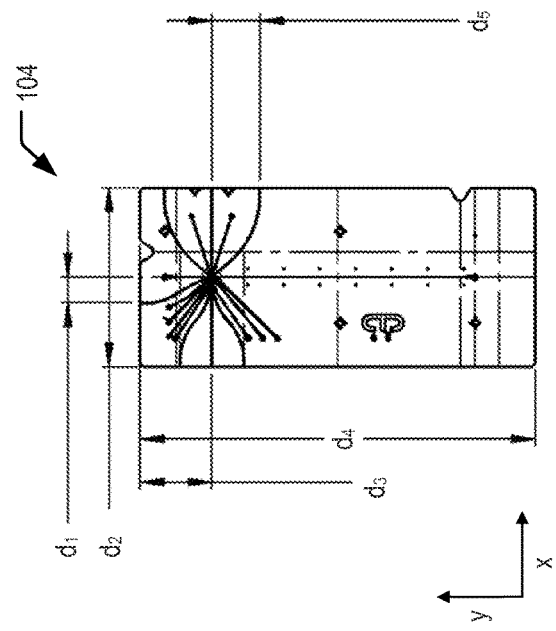
Figure 12C:
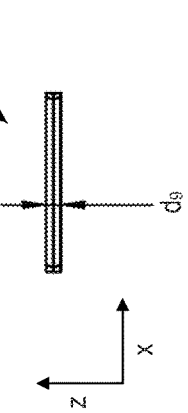

In order to detect scattering from single particles, it may be useful to provide a laser excitation beam that is narrower than the interparticle spacing of cells travelling within the flow-cell. This sets an upper limit on the 1/e (about 0.368) multiplied by the half-width of the laser excitation beam of about 20 μm (y-axis of FIG. 11). The flow cell used in the cytometer focuses cells having a diameter of at least about 5 μm in two spatial positions across the width of the channel as described below. Cells with a diameter of less than about 5 μm were considered to be randomly distributed throughout the flow cell cross-section. Because of this orientation, it may be useful to provide a laser excitation beam that is homogeneous across the width and height of the channel (x- and z-axes of FIG. 11, respectively). In one aspect, a homogenous beam distribution may ensure that cells and particles within the flow cell receive uniform excitation. Moreover, it may be useful to provide a beam depth of focus (DOF) greater than or equal to the width of the channel.

In another aspect, the optical system was configured to collect scattered light at specific angles with respect to the incident beam. Based on scattering cross-sections calculated using Mie theory, the optical system was selected for the detection of signals from particles with a scattering cross-section ranging from about 0.006 μm² to about 5 μm². In addition to forward scattering, optics were positioned to collect ALL of the incident laser beam. ALL may be used to determine both cell size as well as extinction of the laser beam due to optical absorption. The absorption measurement was used to differentiate cells by staining cells with absorptive dyes. Detection optics were used to collect side scatter and fluorescence signals at angles close to 90 degrees perpendicular to the excitation beam.

The flow cell spatially localized and separated cells or particles before optical analysis. In one aspect, particle enumeration errors may result from multiple particles within the sensing region. Therefore, the flow cell was designed to localize the individual particles for the CBC within the ATE limits. Particle localization in the channel was accomplished with inertial flow focusing. Inertial focusing of cells in a 30 µm×55 µm rectangular channel lead to two focal positions within the channel as shown in FIGS. 3A and 3B. Particles focused in channels of this cross section after 30 mm at moderate flow rates (10-100 µL/min). The fluid cell was oriented with respect to the optical system to ensure equal irradiance of both particle positions within the target CV of detection (5%). This flow cell geometry was capable of focusing cells greater than or equal to 5 µm in diameter. Generally, platelets, which are approximately 1.8-3.9 µm in diameter, do not spatially localize along well-defined streamlines and are randomly distributed throughout the channel cross section. For this reason, the excitation beam was configured for uniform intensity along the 55 µm depth of the channel (z-axis; see FIGS. 3A and 3B).

To achieve the aforementioned design requirements, an ICM was designed that contained both the optics and fluidics (FIGS. 12A-12D and 13A-13B). The ICM was a planar device with the fluidics and optics integrated onto a single substrate or chip. The ICM was one component of a fixed analyzer system. The module was designed to be replaceable, but capable of performing thousands of assays without failure. The fluid structures were rectangular microfluidic channels that acted to align cells with respect to one or more optical excitation sources. The optical sources and scattering signals were directed to the fluidic circuit through a series of waveguides and optical focusing elements. The waveguides and focusing optics were integrated on the chip to simplify the alignment of the optical sources with the chip as well as to align the angle-dependent scattering signals with the detection elements.

The design of the optical system for the ICM, was split into excitation and detection subsystem designs. The excitation system guides light from a laser source to a lens element that is molded into the ICM substrate that acts to focus the beam within the requirements listed in Table 4. The detection subsystem recollimates the excitation source and collects and guides the scattered light into different detectors, which measure the scattered light intensity. This intensity was used to count and classify the cells listed in Table 3.

TABLE 4

| | Parameter | Specification |
|---|---|---|
| optical inputs: | Maximum beam ½ width y-axis | 20.0 µm |
| | Beam intensity variation across x-axis | <5% across 30 µm flow channel width |
| | Wavelength | 640 nm |
| | Maximum input power | 25 mW |
| flow cell geometry: | Flow channel cross-sectional width | 30 µm |
| | Flow channel cross-sectional height | 55 µm |
| | Flow cell substrate thickness | 2.2 mm |
| Particle parameters: | Inter-particle spacing within flow channel for focused cells >5 µm diameter | 30 µm center to center |
| | Focused cell position within channel | See FIGS. 3A and 3B |
| | Smallest calculated scattering cross section | 0.006 µm² |

TABLE 4-continued

| | Parameter | Specification |
|---|---|---|
| | Largest calculated scattering cross section | 5 µm² |
| Cytometer module size: | Module length | 12.7 cm (5 inches) |
| | Module width | 7.62 cm (3 inches) |
| | Module height | 7.62 cm (3 inches) |

The design of integrated optics and waveguides is dependent upon material properties, and the design tolerances were based on fabrication methods available for a given set of chosen materials. Based on functional requirements for reusability and cost, the ICM was designed as a molded thermoplastic device. The waveguide channels were filled with an optical grade thermal cured epoxy (Epotek 301) core material with a high index of refraction. The cladding was a thermoplastic material (Zeonex 480R COP) having a lower refractive index (Table 5). For the ICM, the core was a square or rectangular cross-section channel 50 µm tall and 30 µm, 50 µm, or 70 µm wide. The ICM was produced in plastic using a soft embossing technique followed by sealing against a backing plate to form the network of fluid channels. This embossing and sealing production method required a minimum of 20 µm distance between embossed features.

TABLE 5

| Core material | Epotek 301 thermal cure optical epoxy |
|---|---|
| Core index of refraction, $n_1$ | 1.554 ± 0.004 @ 587 nm |
| $dn_1/dT$ | −0.0002/° C. |
| Cladding material | Zeonex 480R |
| Cladding index, $n_2$ | 1.525 ± 0.001 @ 587 nm |
| $dn_2/dT$ | −0.0001/° C. |
| $NA_{in}$ | 0.299 |
| $\theta_{max,\,in}$ | 0.303 rad |
| $\theta_{max,\,out}$ | 0.197 rad |

Figure 14:
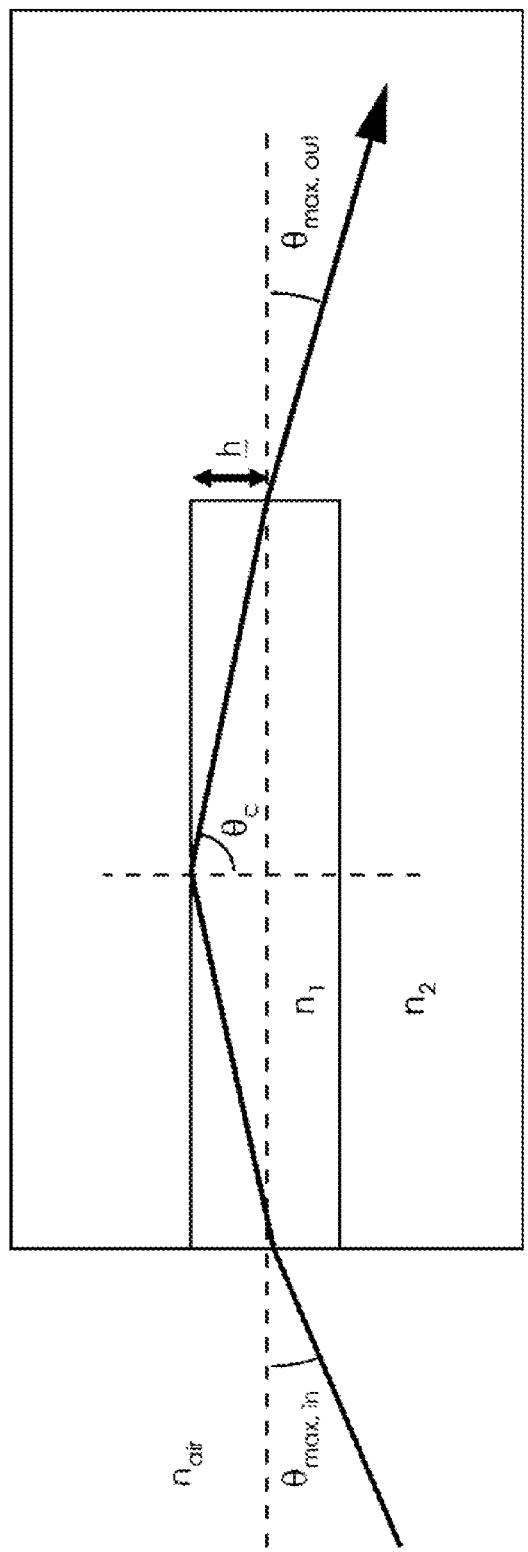
FIG. 14 is a schematic of an example waveguide system.

The waveguide system on the plastic ICM behaved as a multimode, square, step-index waveguide optic (FIG. 14). The waveguides may support many modes of optical light propagation. Further, the waveguides are readily coupled to a light source, thereby enabling alignment with an external source. The multimode system also creates a top-hat intensity profile with a width of 2*h which effectively illuminates the fluid channel across both the width and height as described in the requirements above. In addition to square waveguides, the ICM contains a set of focusing elements that act to concentrate the excitation beam on the sample fluid stream and collimate the beam into the detection elements. These lenses have curved surfaces in the x-y plane, but are straight in the z-plane, and thus act as cylindrical lenses in the plane of the device features.

In the present example multimode ICM waveguide system, rays at angles less than or equal to some critical angle, a, are propagated through the waveguide, while others reflect away from the high index core. The critical input and output angles, $\theta_{max,\,in}$ and $\theta_{max,\,out}$, respectively, describe the largest angles at which rays can enter and exit the system. These angles are determined by the difference between the core and cladding refractive indices, $n_1$ and $n_2$, respectively, and are related to the Numerical Aperture (NA) by Eq. 2:

$$NA = n\sin(\theta_{max}) = \sqrt{n_1^2 - n_2^2} \qquad \text{(Eq. 2)};$$

For a step-index slab waveguide, light propagates both in the plane of the optical elements and out of plane. When light exits the end faces of waveguides, the in-plane light is collimated by the cylindrical optics, but the out of plane light is lost through the top and bottom of the slab. In a slab waveguiding system, it may be useful to minimize the distance between the excitation waveguide end face and the fluid channel (L1+L2+L3) to maximize excitation power at the fluid channel and maximize the signal to noise ratio of the scattering measurement. For the materials listed in Table 5, the fractional light loss out of the top and bottom of the chip is shown in FIG. 4A. The angle of light exiting the waveguide is defined by Eq. 2.

For any optical system, rays from a source with height, h, and slope θ (FIG. 14) can be propagated to an image plane with a new height, h', and slope, θ'. The product of the slope and height is conserved for perfect optical systems as shown in Eq. 3:

$$h\theta = h'\theta' \qquad (Eq. 3);$$

Therefore, for a given starting waveguide half width, h, and numerical aperture, which determines $\theta_{max}$, there is a limit to how tight a beam can be formed within a given divergence angle θ'. Accordingly, the divergence angle may be an important aspect of cytometer system design.

When particles (e.g., cells) interact with light they absorb light as well as scatter the light into different angles as depicted in FIGS. 9 and 10. To differentiate cells from one another, the scattered light must be measured separately from the extinction of the primary excitation field (i.e., scatter is measured in a darkfield optical system). The divergence angle, θ', therefore determines the smallest scatter angles that can be measured.

The geometrical elements in the optical path of the ICM were modeled and optimized using computation and analysis software (Zemax and Matlab). The surfaces for the excitation lens were modeled as two aspheric surfaces. The shapes of these surfaces were altered based on a merit function which attempted to minimize the total beam width at the center of the fluid channel, maximize the amount of light collected from the excitation waveguide, while keeping all distances between optic surfaces to greater than about 20 μm. For the model, the input light source was modeled as a ray bundle with a random spatial distribution across the geometry constraints of the waveguide and with a random angular distribution contained within the critical angle of the system as defined in Eq. 2. For the integrated cytometry device, with optimized excitation lens, the total length from excitation waveguide to fluid channel was 81 μm, corresponding to reduction of excitation intensity at the fluid channel of 25%, as shown in FIG. 4B. The optimized geometry parameters for the aspheric surfaces are listed in Table 6.

TABLE 6

| Aspheric Surface | Conic Constant (mm) | Radius (mm) | Diameter (mm) |
|---|---|---|---|
| $A_1$ | −30.44 | 0.080 | 0.052 |
| $A_2$ | −0.025 | 0.028 | 0.130 |
| $A_3$ | −0.787 | 0.055 | 0.240 |
| $A_4$ | −0.106 | 0.237 | 0.400 |

Figure 15A:
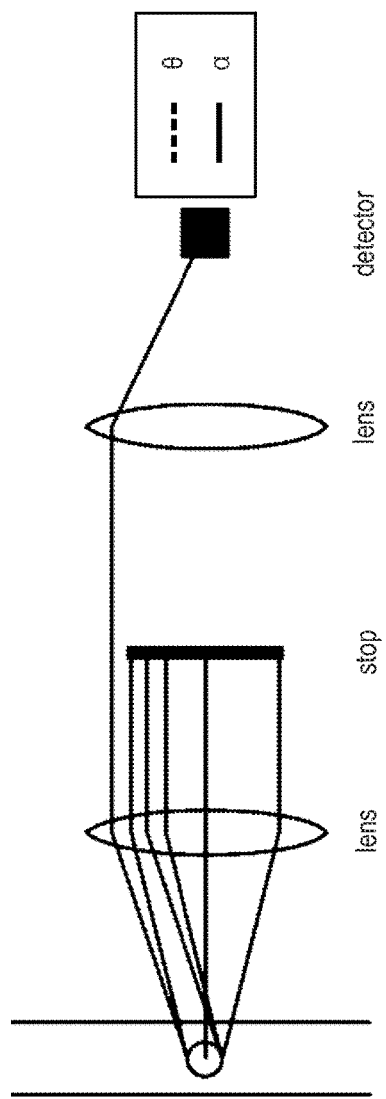
FIGS. 15A-15B are a schematic illustration of the design of an example darkfield optical system.
Figure 15B:
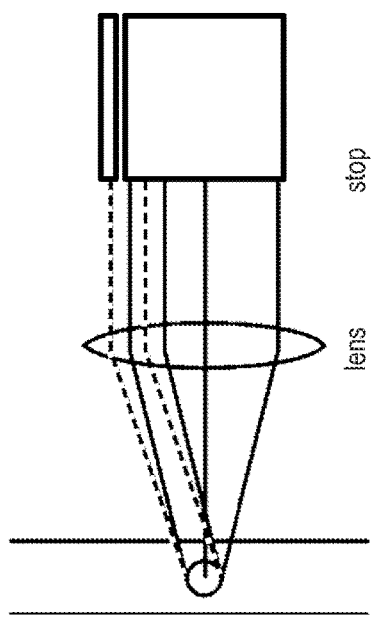

Scattering of light by particles in the CBC was dominated by Mie scattering theory (FIGS. 9 and 10). As presented in Table 4, the ICM may be capable of measuring cells and particles with a differential scattering cross section as small as 0.006 μm². For an incident beam with an irradiance of 1 mW/μm², the scattered light is 6 μW, or 0.6% of the incident beam. To detect this scattered light, it may be separated from the incident beam (see FIGS. 15A and 15B). For the ICM, the scattered light was separated from the incident beam in a pseudo-darkfield optical system.

To construct the system described above, 2D raytracing simulations were performed. The excitation lens (Table 3) was not changed, but the collection optic was optimized to collimate the output beam. In particular, the optimization was determined by the minimization of a merit function, which was a weighted sum of the sum of the absolute values of the slopes for all the rays, the maximum transverse displacement of the most extreme ray in the system, and the number of rays clipped by the collection lens (FIGS. 5A and 5B). The beam was mostly collimated following the exit of the second lens. When scattered rays were introduced at the center of the fluid channel, the scattered beam was partially separated from the parent beam. The detection waveguide was placed to capture as much of the offset rays as possible, while limiting contamination by the parent beam.

As shown in FIGS. 12A-12D and 13A-13B, the collection side of the ICM contains the optimized collection optic and three collection waveguide optics. The central waveguide (160 μm wide) is centered on the optic axis and collects the incident beam. The additional waveguides are spaced 20 μm (top) and 40 μm (bottom) from the edges of the central waveguide. Details of the placement of the waveguides and the collection optics (FIGS. 12A-12D and 13A-13B) are provided in Table 7.

TABLE 7

| Dimension | Value (mm) |
|---|---|
| $d_1$ | 3.56 |
| $d_2$ | 25 |
| $d_3$ | 10 |
| $d_4$ | 55 |
| $d_5$ | 6.65896 |
| $d_6$ | 43.17 |
| $d_7$ | 8.42 |
| $d_8$ | 3.42 |
| $d_9$ | 2 |
| $d_{10}$ | 10 |
| $d_{11}$ | 0.024 |
| $d_{12}$ | 0.054 |
| $d_{13}$ | 0.090 |
| $d_{14}$ | 0.301 |
| $d_{15}$ | 0.325 |
| $d_{16}$ | 0.55 |
| $d_{17}$ | 0.05 |
| $d_{18}$ | 0.04 |
| $d_{19}$ | 0.16 |
| $d_{20}$ | 0.02 |
| $d_{21}$ | 0.08 |
| $d_{22}$ | 0.052 |
| $d_{23}$ | 0.24 |
| $d_{24}$ | 0.40 |

Using design features above, ICMs were constructed in both elastomers (PDMS) and thermoplastics (Zeonor 480R). Waveguides were filled with materials ranging in index of refraction between 1.53-1.72. In the present embodiment, the optical performance was best at the design index of refraction of 1.55. For COP devices, the waveguide channels were filled with optical-grade epoxy (Epotek 301 or Epoxyset EB-107LP-1). Light was injected into the waveguides via direct fiber coupling from an external fiber-coupled laser or via a fiber placed directly into the waveguide channels. The width of the beam was measured in the fluid channel and at the different output waveguides. Beam focusing is shown in FIG. 6D. More than 10 devices were characterized and all had a focused beam width measured with fluorescent dye of 15±3 μm measured in the center of the channel. ICMs were used to discriminate and count platelets and RBCs using scatter differentials of the ALL and FSC channels as shown in FIGS. 7E and 7F.

The present invention has been described in terms of one or more preferred embodiments, and it should be appreciated that many equivalents, alternatives, variations, and modifications, aside from those expressly stated, are possible and within the scope of the invention.

Each reference identified in the present application is herein incorporated by reference in its entirety.

While present inventive concepts have been described with reference to particular embodiments, those of ordinary skill in the art will appreciate that various substitutions and/or other alterations may be made to the embodiments without departing from the spirit of present inventive concepts. Accordingly, the foregoing description is meant to be exemplary, and does not limit the scope of present inventive concepts.

A number of examples have been described herein. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the present inventive concepts.

What is claimed is:

1. A microfluidic device for analysis of a plurality of particles, comprising:
    a fluid channel having a geometry configured to effect a predetermined spacing of the particles;
    an excitation waveguide configured to receive an excitation beam from a source to provide the excitation beam to the fluid channel;
    an excitation lens arranged to receive the excitation beam directed toward the fluid channel and configured to focus the excitation beam to a predetermined width that is less than the predetermined spacing of the particles in the fluid channel to induce an interaction between the excitation beam and the particles resulting in a transmitted light;
    a detection lens arranged relative to the transmitted light and configured to guide the transmitted light along a plurality of paths;
    at least one scattered light waveguide configured to receive light scattered by the particles;
    an axial light loss waveguide configured to receive light guided by the detection lens along at least one of the plurality of paths and not received by the at least one scattered light waveguide;
    a detector arranged to receive transmitted light from the at least one scattered light waveguide and from the axial light loss waveguide and generate a detection signal based thereon; and
    a processor configured to receive the detection signal and determine characteristic features of each of the plurality of particles based on the detection signal.

2. A microfluidic device for analysis of a plurality of particles, comprising:
    a fluid channel having a geometry relative to the plurality of particles configured to effect a predetermined spacing of the particles;
    an excitation waveguide configured to receive an excitation beam from a source to provide the excitation beam to the fluid channel;
    an excitation lens arranged to receive the excitation beam directed toward the fluid channel and configured to focus the excitation beam to a predetermined width that is less than the predetermined spacing of the particles in the fluid channel to induce an interaction between the excitation beam and the particles resulting in a transmitted light;
    a detection lens arranged relative to the transmitted light and configured to guide the transmitted light along a plurality of paths;
    at least one scattered light waveguide configured to receive light scattered by the particles, the at least one scattered light waveguide further configured to interface with a detector; and
    an axial light loss waveguide configured to receive light guided by the detection lens along at least one of the plurality of paths and not received by the at least one scattered light waveguide, the axial light loss waveguide further configured to interface with the detector.

3. The microfluidic device of claim 2, wherein the scattered light waveguide comprises at least one forward scatter waveguide to receive light guided by the detection lens along at least one of the plurality of paths.

4. The microfluidic device of claim 3, wherein the scattered light waveguide comprises at least one side scatter waveguide to receive light at a high scatter angle relative to an optical axis of the system and greater than angles collected by the at least one forward scatter waveguide and the axial light loss waveguide.

5. The microfluidic device of claim 2, wherein at least one surface of the excitation lens and the detection lens is an aspheric surface.

6. The microfluidic device of claim 4, wherein the side scatter waveguide is oriented between about 45 and about 180 degrees to the optical axis.

7. The microfluidic device of claim 4, wherein the side scatter waveguide is used to collect fluorescently scattered light.

8. The microfluidic device of claim 2, wherein the particles are biological molecules selected from the group consisting of red blood cells, white blood cells, and platelets.

9. The microfluidic device of claim 2, wherein the particles are fluorescent.

10. The microfluidic device of claim 9, wherein the particles are synthetic micro particles.

11. The microfluidic device of claim 10, wherein the synthetic microparticles are selected from polymer microspheres and magnetic microspheres.

12. The microfluidic device of claim 2, wherein the particles are cells.

13. The microfluidic device of claim 2, where the particles are labeled with fluorescent molecules.

14. The microfluidic device of claim 13, where the fluorescent molecules are biological molecules.

15. The microfluidic device of claim 14, wherein the biological molecules are selected from the group consisting of antibodies, oligonucleotides, polypeptide molecules, fluorescent proteins, avidin and its derivatives, and protein G and its derivatives.

16. The microfluidic device of claim 2, wherein a transverse cross-section of the fluid channel is rectangular.

17. The microfluidic device of claim 2, wherein the excitation waveguide, the at least one scattered light wave guide, and the axial light loss waveguide are step-index waveguides comprising a first and second material, and
    wherein a refractive index of the first material is greater than a refractive index of the second material.

18. The microfluidic device of claim 2, wherein at least one of the excitation waveguide, the at least one scattered light waveguide and the axial light loss waveguide comprises a round waveguide inserted into a channel, and
wherein each round waveguide is made up of step index or gradient index optical fibers.

19. The microfluidic device of claim 2, wherein the predetermined spacing of the particles is effected by inertial focusing.

20. The microfluidic device of claim 2, wherein the detector generates a detection signal based on light received from the at least one scattered light waveguide and the axial light loss waveguide and is configured to interface with a processor, the processor configured to receive the detection signal and determine characteristic features of each of the plurality of particles based on the detection signal.

21. The microfluidic device of claim 2, wherein at least one of the excitation lens and the detection lens includes a surface defined by:

$$z(r) = \frac{cr^2}{1 + \sqrt{1 - (1+k)c^2 r^2}} + \sum_{i=4,6,8,\ldots} A_i r^i;$$

wherein z(r) is a surface profile as a function of distance off an optical axis, r, of the at least one of the excitation lens and the detection lens surface curvature,
wherein c is an inverse of a spherical radius of curvature of the at least one of the excitation lens and the detection lens,
wherein k is a conic constant, and
wherein $A_i$ are higher order correction terms.

22. The microfluidic device of claim 2, further comprising:
a series of external optics configured to collect light scattered from the fluid channel and guide the light along a plurality of paths;
an external optical system arranged relative to the transmitted light to guide the transmitted light along a plurality of paths;
at least one set of external optics that receive light guided by the detection lens along at least one of the plurality of paths, configured to interface with one of the detector and another detector;
at least one set of external optics that receive light at a high scatter angle relative to an optical axis of the system to receive transmitted light from at least one scattered light optical path and from an axial light loss optical path and generate a detection signal based thereon; and
a processor configured to receive the detection signal and determine characteristic features of each of the plurality of particles based on the detection signal.

23. A microfluidic device for analysis of a plurality of particles, comprising:
a fluid channel having a geometry configured to effect a predetermined spacing of the particles;
a series of external optics configured to collect light from a source to provide an excitation beam to the fluid channel;
an excitation lens arranged to receive the excitation beam directed toward the fluid channel and configured to focus the excitation beam to a predetermined width that is less than the predetermined spacing of the particles in the fluid channel to induce an interaction between the excitation beam and the particles resulting in a transmitted light;
a detection lens arranged relative to the transmitted light and configured to guide the transmitted light along a plurality of paths;
at least one forward scatter waveguide configured to receive light guided by the detection lens along at least one of the plurality of paths;
an axial light loss waveguide configured to receive light guided by the detection lens along at least one of the plurality of paths and not received by the at least one forward scatter waveguide;
at least one waveguide configured to receive light at a high scatter angle relative to an optical axis of the system and greater than angles collected by the at least one forward scatter waveguide and the axial light loss waveguide;
a detector arranged to receive transmitted light from the at least one forward scatter waveguide and from the axial light loss waveguide and generate a detection signal based thereon; and
a processor configured to receive the detection signal and determine characteristic features of each of the plurality of particles based on the detection signal.

* * * * *

UNITED STATES PATENT AND TRADEMARK OFFICE
CERTIFICATE OF CORRECTION

PATENT NO. : 10,139,333 B2
APPLICATION NO. : 15/032463
DATED : November 27, 2018
INVENTOR(S) : Kenneth T. Kotz et al.

It is certified that error appears in the above-identified patent and that said Letters Patent is hereby corrected as shown below:

In the Specification

Column 1, Line 12, "ail" should be --all--.

Column 6, Line 34, "52" should be --$\Omega$--.

Signed and Sealed this
Eighth Day of January, 2019

Andrei Iancu
*Director of the United States Patent and Trademark Office*